(12) United States Patent
He et al.

(10) Patent No.: US 8,779,168 B2
(45) Date of Patent: Jul. 15, 2014

(54) LACTONE COMPOUNDS AND MATERIALS MADE THEREFROM

(75) Inventors: Meng He, Murrysville, PA (US); Darrin R. Dabideen, Pittsburgh, PA (US); Ruisong Xu, Murrysville, PA (US); Anil Kumar, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 13/313,602

(22) Filed: Dec. 7, 2011

(65) Prior Publication Data

US 2012/0157677 A1    Jun. 21, 2012

Related U.S. Application Data

(60) Provisional application No. 61/459,675, filed on Dec. 16, 2010.

(51) Int. Cl.
*C07D 307/02*    (2006.01)
*C07D 307/00*    (2006.01)

(52) U.S. Cl.
USPC .......................................... 549/295; 549/326

(58) Field of Classification Search
USPC .................................................. 549/295, 326
See application file for complete search history.

(56) References Cited

U.S. PATENT DOCUMENTS

| | | |
|---|---|---|
| 3,361,706 A | 1/1968 | Meriwether et al. |
| 3,562,172 A | 2/1971 | Ono et al. |
| 3,567,605 A | 3/1971 | Becker |
| 3,578,602 A | 5/1971 | Ono et al. |
| 4,215,010 A | 7/1980 | Hovey et al. |
| 4,342,668 A | 8/1982 | Hovey et al. |
| 4,637,698 A | 1/1987 | Kwak et al. |
| 4,816,584 A | 3/1989 | Kwak et al. |
| 4,818,096 A | 4/1989 | Heller et al. |
| 4,826,977 A | 5/1989 | Heller et al. |
| 4,880,667 A | 11/1989 | Welch |
| 4,931,219 A | 6/1990 | Kwiatkowski et al. |
| 4,931,220 A | 6/1990 | Haynes et al. |
| 5,066,818 A | 11/1991 | Gemert et al. |
| 5,238,931 A | 8/1993 | Yoshikawa et al. |
| 5,274,132 A | 12/1993 | VanGemert |
| 5,384,077 A | 1/1995 | Knowles |
| 5,405,958 A | 4/1995 | VanGemert |
| 5,466,398 A | 11/1995 | Van Gemert et al. |
| 6,068,797 A | 5/2000 | Hunt |
| 6,555,028 B2 | 4/2003 | Walters et al. |
| 2009/0323011 A1 | 12/2009 | He et al. |

FOREIGN PATENT DOCUMENTS

| | | |
|---|---|---|
| DE | 199 02 771 A1 | 12/1999 |
| WO | 00/14082 A1 | 3/2000 |
| WO | 2010/065393 A1 | 6/2010 |

OTHER PUBLICATIONS

STN Accession No. 1993:538999 Document No. 119:138999 Abstract of Lehmann, Archiv der Pharmazie (Weinheim, Germany) (1993), 326(5), 291-6.*
STN Accession No. 1967:508574 Document No. 67:108574 Abstract of Lewis et al. Tetrahedron (1967), 23(11), 4197-208.*
Dorwald F. A. Side Reactions in Organic Synthesis, 2005, Wiley: VCH, Weinheim pg. IX of Preface p. 1-15.*
Sarvari et al.; "Reactions on a Solid Surface. A Simple, Economical and Efficient Friedel-Crafts Acylation Reaction over Zinc Oxide (ZnO) as a New Catalyst"; J. Org. Chem.; Aug. 28, 2004; pp. 6953-6956; vol. 69; American Chemical Society.
Muraoka et al.; "Accentuation of the DI-(pi)-Methane Reactivity by Central Carbon Substitution in the 4-(Phenylmethyl)-2(5H)-Furanone System"; Heterocycles; 1990; pp. 1589-1592; vol. 31, No. 9.

(Continued)

*Primary Examiner* — Nizal Chandrakumar
(74) *Attorney, Agent, or Firm* — The Webb Law Firm

(57) ABSTRACT

The present invention relates to lactone compounds represented by the following Formulas I and II, and methods of making such lactone compounds.

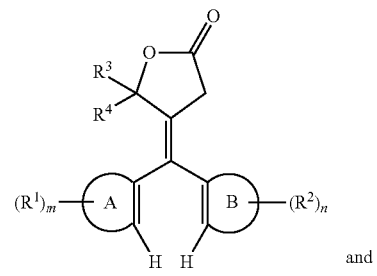

and

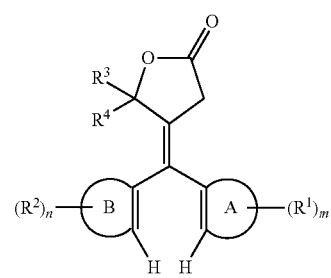

The present invention also relates to methods of making other materials from such lactone compounds, such as fused ring indenol compounds (e.g., indeno-fused naphthols), and fused ring indenopyran compounds (e.g., indeno-fused naphthopyrans).

5 Claims, No Drawings

(56) References Cited

OTHER PUBLICATIONS

Muraoka et al.; "Furan-2(3H)- and -2(5H)-Ones. Part 6. Di-{pi}-Methane Rearrangement of the (alpha)-Substituted 4-Benzylfuran-2(5H)-One System"; J. Chem. Soc. Perkin Trans; 1995; pp. 1437-1443; XP009156689.

Lehmann et al.; "'Y-Lactonisierte' Neuroleptika—Synthese, Stereochemie und Affinitat am D2-Rezeptor"; Arch. Pharm.; 1993; pp. 291-296, vol. 326; Weinheim.

Hawley's Condensed Chemical Dictionary, Thirteenth Edition, 1997, John Wiley & Sons, pp. 901-902.

* cited by examiner

LACTONE COMPOUNDS AND MATERIALS MADE THEREFROM

CROSS REFERENCE TO RELATED APPLICATION

This application claims the benefit of U.S. Provisional Patent Application No. 61/459,675, filed on Dec. 16, 2010.

FIELD OF THE INVENTION

The present invention relates to lactone compounds, such as fused ring lactone compounds, methods of making lactone compounds, and methods of making other materials, such as fused ring indenol compounds and fused ring indenopyran compounds, from lactone compounds.

BACKGROUND OF THE INVENTION

Fused ring indenol compounds, such as indeno-fused naphthols, have many uses, such as intermediates in the synthesis of photochromic compounds and materials, such as fused ring indenopyrans, including indeno-fused naphthopyrans. Photochromic materials, such as indeno-fused naphthopyrans, in response to certain wavelengths of electromagnetic radiation (or "actinic radiation"), typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, e.g., substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (e.g., in form of a photochromic coating composition) typically display colorless (e.g., clear) and colored states that correspond to the colorless and colored states of the photochromic materials contained therein or applied thereto.

Indeno-fused naphthol materials are typically prepared by a synthetic scheme involving the reaction of a benzophenone with a dialkyl succinate, which is typically referred to as a Stobbe reaction route. When unsymmetrical benzophenones are used, a mixture of indeno-fused naphthol materials typically results from the Stobbe reaction route. The mixture of indeno-fused naphthols typically must be separated so as to isolate the desired indeno-fused naphthol. The isolated indeno-fused naphthol can then be used in subsequent reactions (e.g., in the synthesis of photochromic indeno-fused naphthopyrans). The separation and isolation steps generally result in significantly reduced yields relative to the desired indeno-fused naphthol materials. In addition, the Stobbe reaction route can involve two separate ring closure steps, which are typically conducted at separate times and in separate reaction vessels.

Some photochromic materials, such as photochromic indeno-fused naphthopyrans can be expensive, and in light of economic considerations, reducing the costs associated with synthesizing such materials is typically desirable.

It would be desirable to develop new materials, such as intermediates, and new methods of using such newly developed materials, to make, for example, indeno-fused naphthols and related materials. In addition, it would be desirable that such newly developed materials and methods provide improvements, such as, higher yields, a reduced number of synthetic steps, and reduced costs relative to previous synthetic methods.

SUMMARY OF THE INVENTION

In accordance with the present invention, there is provided a lactone compound selected from lactone compounds represented by at least one of the following Formula I and Formula II,

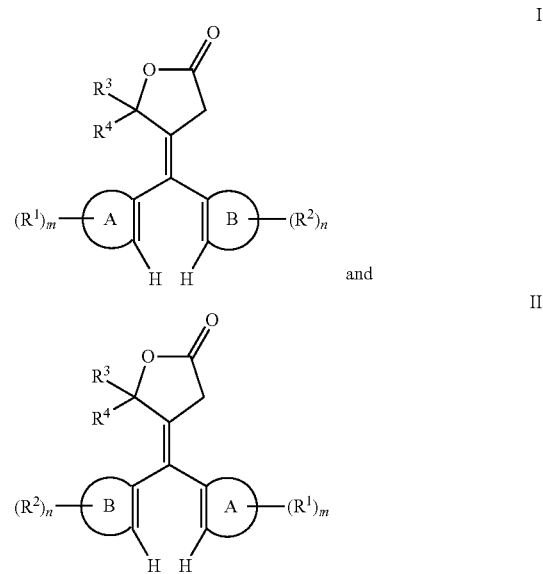

With reference to Formulas I and II, Ring-A and Ring-B are each independently selected from unsubstituted aryl, substituted aryl, unsubstituted fused ring aryl, substituted fused ring aryl, unsubstituted heteroaryl, and substituted heteroaryl.

With further reference to Formulas I and II, m and n are each independently selected from 0 to a value corresponding to as many positions on Ring-A and Ring-B, respectively, to which an $R^1$ group or an $R^2$ group can be bonded. Typically, m and n are each independently 0 to 4. Ring-A positions to which an $R^1$ group is not bonded, can instead have hydrogen groups bonded thereto. Similarly, Ring-B positions to which an $R^2$ group is not bonded, can instead have hydrogen groups bonded thereto. In addition, $R^1$ for each m, and $R^2$ for each n, are in each case independently selected from: hydrocarbyl optionally interrupted with at least one of —O—, —S—, —C(O)—, —C(O)O—, —S(O)—, —SO$_2$—, —N($R_{11}$')— where $R_{11}$' is selected from hydrogen, hydrocarbyl or substituted hydrocarbyl, and combinations of two or more thereof; substituted hydrocarbyl optionally interrupted with at least one of —O—, —S—, —C(O)—, —C(O)O—, —S(O)—, —SO$_2$—, —N($R_{11}$')— where $R_{11}$' is selected from hydrogen, hydrocarbyl or substituted hydrocarbyl, and combinations of two or more thereof; halogen; cyano; and —N($R_{11}$')$R_{12}$', wherein $R_{11}$' and $R_{12}$' are each independently selected from hydrogen, hydrocarbyl or substituted hydrocarbyl, or $R_{11}$' and $R_{12}$' together form a ring structure optionally including at least one heteroatom.

The $R^3$ and $R^4$ groups of Formulas I and II are each independently selected from: hydrogen; hydrocarbyl optionally interrupted with at least one of —O—, —S—, —C(O)—, —C(O)O—, —S(O)—, —SO$_2$—, and —N(R$_{11}$')— where R$_{11}$' is selected from hydrogen, hydrocarbyl or substituted hydrocarbyl; and substituted hydrocarbyl optionally interrupted with at least one of —O—, —S—, —C(O)—, —C(O)O—, —S(O)—, —SO$_2$—, and —N(R$_{11}$')— where R$_{11}$' is selected from hydrogen, hydrocarbyl or substituted hydrocarbyl; or R$^3$ and R$^4$ together form a ring structure optionally including at least one heteroatom. One or more of R$^1$, R$^2$, R$^3$ and R$^4$ can in each case independently represent one or more precursors of those groups as described above and further herein with reference to, for example, Formulas I and II.

In accordance with the present invention, there is further provided a method of making a fused ring indenol compound represented by at least one of the following Formula III and Formula III-2,

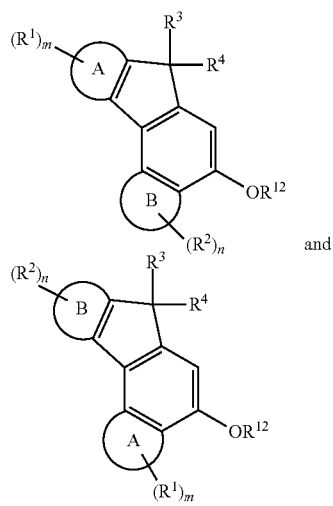

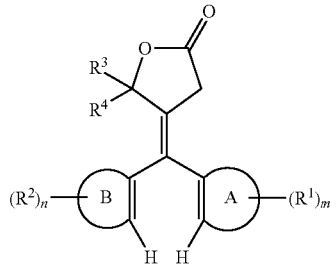

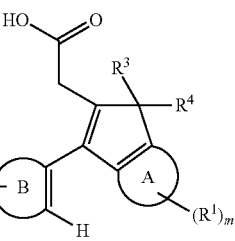

With reference to Formulas III and III-2, Ring-A, Ring-B, m, n, R$^1$, R$^2$, R$^3$ and R$^4$ are each as previously described herein with regard to the lactone compounds represented by Formulas I and II. Alternatively, one or more of R$^1$, R$^2$, R$^3$ and R$^4$ can in each case independently represent one or more precursors of those groups as described above and further herein with reference to, for example, Formulas I and II. The R$^{12}$ group of Formulas III and III-2 is selected from hydrogen, —C(O)—R$^{13}$ and —S(O)(O)R$^{13}$, wherein R$^{13}$ is selected from hydrocarbyl and halohydrocarbyl.

The method of making the fused ring indenol compound represented by Formulas III and III-2 comprises, converting a lactone compound selected from lactone compounds represented by at least one of the following Formulas I and II, to an acid intermediate comprising an acid intermediate represented by at least one of Formula IV and Formula IV-2,

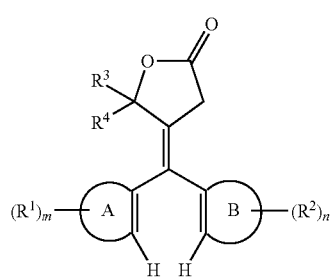

The method of making the fused ring indenol compound represented by Formula III or III-2, further comprises, converting the acid intermediate represented by Formula IV or IV-2 to the corresponding indeno-fused ring compound represented by Formula III or III-2.

The present invention also provides a method of forming the lactone compound represented by at least one of Formulas I and II, as described above. The method comprises, reacting an acid ester represented by at least one of Formula VI and Formula VII with at least one of (i) a metal hydride reducing agent, and/or (ii) a nucleophile represented by at least one of Formula VIII and Formula IX, thereby forming the lactone compound. Representations of Formulas VI, VII, VIII and IX are provided as follows:

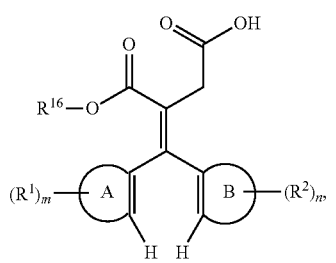

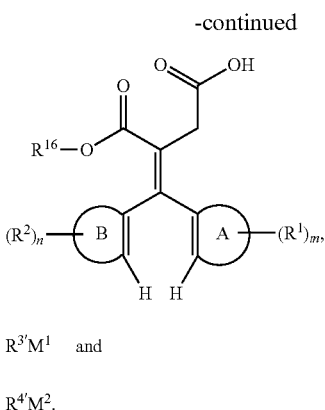

VII

VIII R³'M¹ and

IX R⁴'M².

With reference to Formulas VI, VII, VIII and IX: $R^{16}$ is selected from hydrocarbyl and substituted hydrocarbyl; $R^{3'}$ is a nucleophile of $R^3$ as described with reference to Formulas I and II; $R^{4'}$ is a nucleophile of $R^4$ as described with reference to Formulas I and II; and $M^1$ and $M^2$ are each independently selected from $Si(R^{18})_3$, where each $R^{18}$ is independently selected from $C_1$-$C_8$ alkyl, or $M^1$ and $M^2$ each independently represent a counterion comprising a metal selected from Mg, Li, Mn, Cu, Zn, Al, Ti, Ln, and combinations thereof.

There is further provided, in accordance with the present invention, a method of making fused ring indenopyran compounds represented by the following Formulas X and X-2,

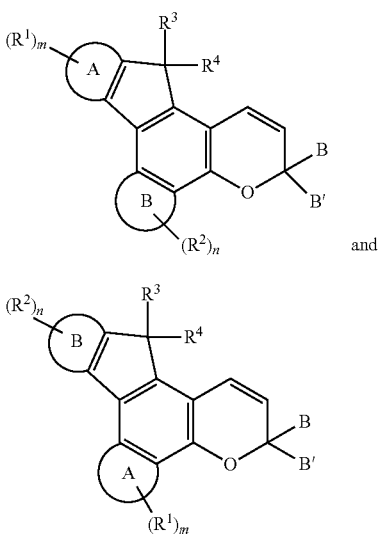

X and

X-2

With reference to Formulas X and X-2, Ring-A, Ring-B, m, n, $R^1$, $R^2$, $R^3$ and $R^4$ are each as previously described herein, for example, with regard to the lactone compounds represented by Formulas I and II. Alternatively, one or more of $R^1$, $R^2$, $R^3$ and $R^4$ can in each case independently represent one or more precursors of the those groups as described above and further herein with reference to, for example, Formulas I, II, III and III-2.

The B and B' groups of Formulas X and X-2 are each independently selected from unsubstituted aryl, substituted aryl, unsubstituted heteroaryl, substituted heteroaryl, polyalkoxy, and polyalkoxy having a polymerizable group. Alternatively B and B', of Formulas X and X-2, taken together can form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring.

The method of forming the fused ring indenopyran compound represented by Formulas X and X-2 comprises, converting a lactone compound selected from lactone compounds represented by at least one of Formula I and Formula II, to an acid intermediate comprising an acid intermediate represented by at least one of Formulas IV and IV-2, each as described previously herein. The method further comprises converting the acid intermediate represented by Formula IV and/or IV-2 to a corresponding fused ring indenol compound represented by Formula III and/or III-2, as described previously herein.

The method of forming the compound represented by Formula X or X-2 further comprises, reacting the fused ring indenol compound represented by at least one of Formula III and III-2 with a propargyl alcohol represented by the following Formula XI,

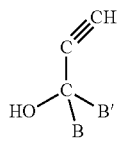

XI

The compound represented by Formulas X and/or X-2 is thereby formed. The B and B' groups of the propargyl alcohol represented by Formula XI, are each as described previously herein with regard to the compound represented by Formula X or X-2. Alternatively, one or more of the B and B' groups of Formula XI, can in each case independently represent one or more precursors of the those groups as described above and further herein with reference to, for example, Formula X or X-2.

DETAILED DESCRIPTION OF THE INVENTION

As used herein and in the claims, the term "actinic radiation" means electromagnetic radiation that is capable of transforming a photochromic material from one form or state to another.

As used herein and in the claims, the term "photochromic" means having an absorption spectrum for at least visible radiation that varies in response to absorption of at least actinic radiation. Further, as used herein the term "photochromic material" means any substance that is adapted to display photochromic properties, i.e. adapted to have an absorption spectrum for at least visible radiation that varies in response to absorption of at least actinic radiation, and which includes at least one photochromic compound.

As used herein and in the claims, recitations of "linear or branched" groups, such as linear or branched alkyl, are understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein and in the claims, the term "halo" and similar terms, such as halo group, halogen, and halogen group means F, Cl, Br and/or I, such as fluoro, chloro, iodo, bromo and/or iodo.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein and in the claims, the articles "a," "an," and "the" include plural referents unless otherwise expressly and unequivocally limited to one referent.

Other than in the operating examples, or where otherwise indicated, all numbers expressing quantities of ingredients, reaction conditions, and so forth used in the specification and claims are to be understood as modified in all instances by the term "about."

Various groups of the compounds and intermediates described previously and further herein, for example the $R^1$, $R^2$, $R^3$ and $R^4$ groups of the lactone compounds represented by Formulas I and II, can in each case be independently selected from hydrocarbyl and substituted hydrocarbyl.

As used herein and in the claims the term "hydrocarbyl" and similar terms, such as "hydrocarbyl substituent" and "hydrocarbyl group" means: linear or branched $C_1$-$C_{20}$ alkyl (e.g., linear or branched $C_1$-$C_{10}$ alkyl); linear or branched $C_2$-$C_{20}$ alkenyl (e.g., linear or branched $C_2$-$C_{10}$ alkenyl); linear or branched $C_2$-$C_{20}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to tetrahydrofuranyl, tetrahydropyranyl and piperidinyl. Representative aryl groups include but are not limited to phenyl and naphthyl. Representative heteroaryl groups include but are not limited to furanyl, pyranyl and pyridinyl. Representative aralkyl groups include but are not limited to benzyl, and phenethyl.

The term "substituted hydrocarbyl" as used herein and in the claims means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —N($R_{11}'$)($R_{12}'$) where $R_{11}'$ and $R_{12}'$ are each independently selected from hydrogen, hydrocarbyl and substituted hydrocarbyl, or $R_{11}'$ and $R_{12}'$ together form a cyclic ring optionally including at least one heteroatom (e.g., —O— and/or —S—).

The term "substituted hydrocarbyl" is inclusive of halohydrocarbyl (or halo substituted hydrocarbyl) substituents. The term "halohydrocarbyl" as used herein and in the claims, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom being replaced by a halogen atom (e.g., a fluoromethyl group) to full halogenation (perhalogenation) in which all replaceable hydrogen atoms on the hydrocarbyl group have been replaced by a halogen atom (e.g., trifluoromethyl or perfluoromethyl). Correspondingly, the term "perhalohydrocarbyl group" as used herein and in the claims means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which various groups and substituents, such as $R^1$, $R^2$, $R^3$ and $R^4$, can each be selected, can in each case be independently and optionally interrupted with at least one of —O—, —S—, —C(O)—, —C(O)O—, —S(O)—, —$SO_2$—, —N($R_{11}'$)—. As used herein and in the claims, by interrupted with at least one of —O—, —S—, —C(O)—, —C(O)O—, —S(O)—, —$SO_2$—, —N($R_{11}'$)—, means that at least one carbon of, but less than all of the carbons of, the hydrocarbyl group or substituted hydrocarbyl group, is in each case independently replaced with one of the recited divalent linking groups. The hydrocarbyl and substituted hydrocarbyl groups can be interrupted with two or more of the above recited linking groups, which can be adjacent each other or separated by one or more carbons.

As used herein and in the claims, recitations of "linear or branched" or "linear, branched or cyclic" groups, such as linear or branched alkyl, or linear, branched or cyclic alkyl, are herein understood to include a methylene group, groups that are linear, such as linear $C_2$-$C_{25}$ alkyl groups, groups that are appropriately branched, such as branched $C_3$-$C_{25}$ alkyl groups, and groups that are appropriately cyclic, such as $C_3$-$C_{25}$ cycloalkyl (or cyclic alkyl) groups.

As used herein and in the claims, the term "precursor" and related terms, such as "precursors" with regard to the various groups, for example, $R^1$, $R^2$, $R^3$, $R^4$, B and B', of the compounds and intermediates described herein, for example, the fused ring compounds represented by Formulas I and II, and the fused ring indenol compounds represented by Formulas III and III-2, means a group that can be converted in one or more steps to the final or desired group. For purposes of non-limiting illustration: a precursor of a hydroxyl group (—OH) includes, but is not limited to, a carboxylic acid ester group (—OC(O)R where R is hydrogen or an optionally substituted hydrocarbyl); and a precursor of a carboxylic acid ester group (—OC(O)R) includes, but is not limited to, a hydroxyl group (—OH), which can be reacted, for example, with a carboxylic acid halide, such as acetic acid chloride (or acetyl chloride).

As used herein and in the claims, unless otherwise indicated, left-to-right representations of linking groups, such as divalent linking groups, are inclusive of other appropriate orientations, such as, right-to-left orientations. For purposes of non-limiting illustration, the left-to-right representation of the divalent linking group —C(O)O—, is inclusive of the right-to-left representation thereof, —O(O)C—.

The groups and substituents of the lactone compounds (e.g., represented by Formulas I and II), the fused ring indenol compounds (e.g., represented by Formula III), the fused ring indenopyran compounds (e.g., represented by Formula X), and the compounds and intermediates used in their preparation, are described in further detail as follows.

The Ring-A and Ring-B groups of the lactone compounds represented by Formulas I and II, can each be independently selected from unsubstituted aryl, substituted aryl, unsubstituted fused ring aryl, substituted fused ring aryl, unsubstituted heteroaryl, and substituted heteroaryl. The substituents of the substituted aryl, fused ring aryl and heteroaryl groups can each be independently selected from hydrocarbyl groups and substituted hydrocarbyl groups, which each can be optionally interrupted with at least one of —O—, —S—, —C(O)—, —C(O)O—, —S(O)—, —SO$_2$—, —N(R$_{11}$')—, as described previously herein. Examples of aryl groups from which Ring-A and Ring-B can each be independently selected include, but are not limited to, phenyl and biphenyl. Examples of fused ring aryl groups from which Ring-A and Ring-B can each be independently selected include, but are not limited to, polycyclic aromatic hydrocarbons, such as naphthyl and anthracenyl. Examples of heteroaryl groups from which Ring-A and Ring-B can each be independently selected include, but are not limited to, furanyl, pyranyl, indolyl, thienyl, benzothienyl, and pyridinyl.

With some embodiments of the present invention, R$^1$ for each m, and R$^2$ for each n, are in each case independently selected from: a reactive substituent; a compatiblizing substituent; halogen selected from iodo, bromo, fluoro and chloro; C$_1$-C$_{20}$ alkyl; C$_3$-C$_{10}$ cycloalkyl; substituted or unsubstituted phenyl; or —O—R$_{10}$' or —C(O)—R$_{10}$' or —C(O)—OR$_{10}$', wherein R$_{10}$' is hydrogen, C$_1$-C$_{20}$ alkyl, phenyl(C$_1$-C$_{20}$)alkyl, mono(C$_1$-C$_{20}$)alkyl substituted phenyl (C$_1$-C$_{20}$)alkyl, mono(C$_1$-C$_{20}$)alkoxy substituted phenyl(C$_1$-C$_{20}$)alkyl, (C$_1$-C$_{20}$)alkoxy(C$_2$-C$_{20}$)alkyl, C$_3$-C$_{10}$ cycloalkyl, or mono(C$_1$-C$_{20}$)alkyl substituted C$_3$-C$_{10}$ cycloalkyl. The phenyl substituents (i.e., the substituents of the substituted phenyl) can be selected from hydroxyl, halogen, carbonyl, C$_1$-C$_{20}$ alkoxycarbonyl, cyano, halo(C$_1$-C$_{20}$)alkyl, C$_1$-C$_{20}$ alkyl or C$_1$-C$_{20}$ alkoxy.

With some further embodiments, R$^1$ for each m, and R$^2$ for each n, are in each case independently and more particularly selected from: C$_1$-C$_6$ alkyl; C$_3$-C$_7$ cycloalkyl; substituted or unsubstituted phenyl; —OR$_{10}$' or —OC(=O)R$_{10}$', wherein R$_{10}$' is hydrogen, C$_1$-C$_6$ alkyl, phenyl(C$_1$-C$_3$)alkyl, mono(C$_1$-C$_6$)alkyl substituted phenyl(C$_1$-C$_3$)alkyl, mono(C$_1$-C$_6$) alkoxy substituted phenyl(C$_1$-C$_3$)alkyl, (C$_1$-C$_6$)alkoxy(C$_2$-C$_4$)alkyl, C$_3$-C$_7$ cycloalkyl, or mono(C$_1$-C$_4$)alkyl substituted C$_3$-C$_7$ cycloalkyl. The phenyl substituents (i.e., the substituents of the substituted phenyl) can be more particularly selected from hydroxyl, halogen, carbonyl, C$_1$-C$_6$ alkoxycarbonyl, cyano, halo(C$_1$-C$_6$)alkyl, C$_1$-C$_6$ alkyl or C$_1$-C$_6$ alkoxy.

Alternatively or in addition to the previously recited classes and examples, R$^1$ for each m, and R$^2$ for each n, can in each case be independently selected from, —N(R$_{11}$')R$_{12}$', wherein R$_{11}$' and R$_{12}$' are each independently hydrogen, C$_1$-C$_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, C$_1$-C$_{20}$ alkylaryl, C$_3$-C$_{10}$ cycloalkyl, C$_4$-C$_{20}$ bicycloalkyl, C$_5$-C$_{20}$ tricycloalkyl or C$_1$-C$_{20}$ alkoxyalkyl, wherein said aryl group is phenyl or naphthyl, or R$_{11}$' and R$_{12}$' come together with the nitrogen atom to form a C$_3$-C$_{20}$ hetero-bicycloalkyl ring or a C$_4$-C$_{20}$ hetero-tricycloalkyl ring.

Further alternatively or in addition to the previously recited classes and examples, R$^1$ for each m, and R$^2$ for each n, can in each case be independently selected from, a nitrogen containing ring represented by the following graphic Formula XIIA,

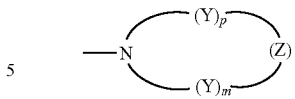

XIIA

With the nitrogen ring substituent represented by general Formula XIIA, each —Y— is independently chosen for each occurrence from —CH$_2$—, —CH(R$_{13}$')—, —C(R$_{13}$')$_2$—, —CH(aryl)-, —C(aryl)$_2$-, and —C(R$_{13}$')(aryl)-, and Z is —Y—, —O—, —S—, —S(O)—, —SO$_2$—, —NH—, —N(R$_{13}$')—, or —N(aryl)-, wherein each R$_{13}$' is independently C$_1$-C$_{20}$ alkyl (e.g., C$_1$-C$_6$ alkyl), each aryl is independently phenyl or naphthyl, m is an integer 1, 2 or 3, and p is an integer 0, 1, 2, or 3 and provided that when p is 0, Z is —Y—.

Additionally or alternatively, R$^1$ for each m, and R$^2$ for each n, can in each case also be independently selected from a nitrogen containing ring substituent represented by general formula XIIB and/or general formula XIIC:

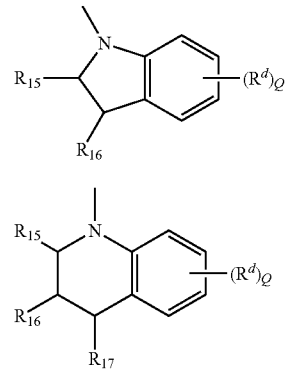

XIIB

XIIC

For the nitrogen containing ring substituents represented by general formulas XIIB and XIIC, R$_{15}$, R$_{16}$, and R$_{17}$ are each independently hydrogen, C$_1$-C$_{20}$ alkyl (e.g., C$_1$-C$_6$ alkyl), phenyl, or naphthyl, or the groups R$_{15}$ and R$_{16}$ together form a ring of 5 to 8 carbon atoms and each Rd is independently for each occurrence selected from C$_1$-C$_{20}$ alkyl (e.g., C$_1$-C$_6$ alkyl), C$_1$-C$_{20}$ alkoxy (e.g., C$_1$-C$_6$ alkoxy), fluoro or chloro, and Q is an integer 0, 1, 2, or 3.

Further alternatively or additionally, R$^1$ for each m, and R$^2$ for each n, can in each case also be independently selected from, unsubstituted, mono-, or di-substituted C$_4$-C$_{18}$ spirobicyclic amine, or unsubstituted, mono-, and di-substituted C$_4$-C$_{18}$ spirotricyclic amine, wherein the substituents are independently aryl, C$_1$-C$_{20}$ alkyl (e.g., C$_1$-C$_6$ alkyl), C$_1$-C$_{20}$ alkoxy (e.g., C$_1$-C$_6$ alkoxy), or phenyl(C$_1$-C$_{20}$)alkyl (e.g., phenyl(C$_1$-C$_6$)alkyl).

With some embodiments of the present invention, two adjacent R$^1$ groups, and/or two adjacent R$^2$ groups, can together form a group represented by the following general formula XIID or general formula XIIE,

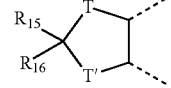

XIID

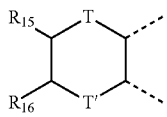

XIIE

With the groups represented by general formulas XIID and XIIE, T and T' are each independently oxygen or the group —NR$_{11}$— where R$_{11}$, R$_{15}$, and R$_{16}$ are each as set forth and described previously herein.

The R$^3$ and R$^4$ groups, with some embodiments of the present invention, can each be independently selected from: a reactive substituent; a compatiblizing substituent; hydrogen; hydroxy; C$_1$-C$_{20}$ alkyl (e.g., C$_1$-C$_6$ alkyl); C$_1$-C$_{20}$ haloalkyl (e.g., C$_1$-C$_6$ haloalkyl); C$_3$-C$_{10}$ cycloalkyl (e.g., C$_3$-C$_7$ cycloalkyl); allyl; benzyl; or mono-substituted benzyl. The benzyl substituents can be chosen from halogen, C$_1$-C$_{20}$ alkyl (e.g., C$_1$-C$_6$ alkyl) or C$_1$-C$_{20}$ alkoxy (e.g., C$_1$-C$_6$ alkoxy).

The R$^3$ and R$^4$ groups with some further embodiments of the present invention, can each be independently selected from, an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl. The group substituents can in each case be independently chosen from halogen, C$_1$-C$_{20}$ alkyl (e.g., C$_1$-C$_6$ alkyl) or C$_1$-C$_{20}$ alkoxy (e.g., C$_1$-C$_6$ alkoxy).

The R$^3$ and R$^4$ groups can also, with some embodiments of the present invention, each be independently selected from a mono-substituted phenyl, in which the phenyl has a substituent located at the para position thereof, which is a linking group, —(CH$_2$)$_t$— or —O—(CH$_2$)$_t$—, that is connected to an aryl group which is a member of a (or another) photochromic material, such as a naphthopyran, an indeno-fused naphthopyran, or benzopyran, and t is chosen from the integer 1, 2, 3, 4, 5 or 6.

Alternatively, the R$^3$ and R$^4$ groups can each be independently selected from the group —CH(R$^{10}$)G, in which R$^{10}$ is hydrogen, C$_1$-C$_{20}$ alkyl (e.g., C$_1$-C$_6$ alkyl) or the unsubstituted, mono- or di-substituted aryl groups phenyl or naphthyl, and G is —CH$_2$OR$^{11}$, in which R$^{11}$ is hydrogen, —C(O)R$^{10}$, C$_1$-C$_{20}$ alkyl (e.g., C$_1$-C$_6$ alkyl), C$_1$-C$_{20}$ alkoxy(C$_1$-C$_{20}$)alkyl (e.g., C$_1$-C$_3$ alkoxy(C$_1$-C$_6$)alkyl), phenyl(C$_1$-C$_{20}$)alkyl (e.g., phenyl(C$_1$-C$_3$)alkyl), mono(C$_1$-C$_{20}$)alkoxy substituted phenyl(C$_1$-C$_{20}$)alkyl (e.g., mono(C$_1$-C$_6$)alkoxy substituted phenyl(C$_1$-C$_3$)alkyl), or the unsubstituted, mono- or di-substituted aryl groups phenyl or naphthyl. The substituents of the phenyl and naphthyl groups can each be independently selected from C$_1$-C$_{20}$ alkyl (e.g., C$_1$-C$_6$ alkyl) or C$_1$-C$_{20}$ alkoxy (e.g., C$_1$-C$_6$ alkoxy).

With some further embodiments of the present invention, R$^3$ and R$^4$ can together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom. The spiro-carbocyclic ring and the spiro-heterocyclic ring are each annellated with 0, 1 or 2 benzene rings. The substituents of the spiro rings can be chosen from hydrogen or C$_1$-C$_{20}$ alkyl (e.g., C$_1$-C$_6$ alkyl).

With some embodiments of the present invention, R$^1$ for each m, and R$^2$ for each n, are in each case independently selected from unsubstituted phenyl, substituted phenyl, C$_1$-C$_6$ alkyl, C$_3$-C$_7$ cycloalkyl, C$_1$-C$_8$ haloalkyl, iodo, bromo, fluoro, chloro, and —O—R$_{10}$'. With further embodiments of the present invention, R$^3$ and R$^4$ are each independently selected from hydrogen, C$_1$-C$_8$ alkyl, C$_1$-C$_8$ haloalkyl, and C$_3$-C$_7$ cycloalkyl, or R$^3$ and R$^4$ together form a spiro substituent selected from a substituted or unsubstituted spiro-carbocyclic ring containing 3 to 6 carbon atoms.

In accordance with some further embodiments, R$^1$ for each m, and R$^2$ for each n, can in each case be independently selected from a group represented by the following Formula XIII, —(S$_1$)$_c$-(Q$_1$-(S$_2$)$_d$)$_{d'}$-(Q$_2$-(S$_3$)$_e$)$_{e'}$-(Q$_3$-(S$_4$)$_f$)$_{f'}$—S$_5$—P    XIII With reference to Formula XIII, Q$_1$, Q$_2$, and Q$_3$ are each independently chosen from, a divalent group chosen from, an unsubstituted or a substituted aromatic group, an unsubstituted or a substituted alicyclic group, an unsubstituted or a substituted heterocyclic group, and mixtures thereof.

The substituents of the substituted aromatic groups, substituted alicyclic groups and substituted heterocyclic groups from which each of Q$_1$, Q$_2$, and Q$_3$ can be selected, are independently chosen from: a group represented by P (as will be described in further detail herein); liquid crystal mesogens; halogen; poly(C$_1$-C$_{18}$ alkoxy); C$_1$-C$_{18}$ alkoxycarbonyl; C$_1$-C$_{18}$ alkylcarbonyl; C$_1$-C$_{18}$ alkoxycarbonyloxy; aryloxycarbonyloxy; perfluoro(C$_1$-C$_{18}$)alkoxy; perfluoro(C$_1$-C$_{18}$)alkoxycarbonyl; perfluoro(C$_1$-C$_{18}$)alkylcarbonyl; perfluoro(C$_1$-C$_{18}$)alkylamino; di-(perfluoro(C$_1$-C$_{18}$)alkyl)amino; perfluoro(C$_1$-C$_{18}$)alkylthio; C$_1$-C$_{18}$ alkylthio; C$_1$-C$_{18}$ acetyl; C$_3$-C$_{10}$ cycloalkyl; C$_3$-C$_{10}$ cycloalkoxy; or a straight-chain or branched C$_1$-C$_{18}$ alkyl group that is mono-substituted with cyano, halo, or C$_1$-C$_{18}$ alkoxy, or poly-substituted with halo.

Additionally or alternatively, the substituents of the substituted aromatic groups, substituted alicyclic groups and substituted heterocyclic groups from which each of Q$_1$, Q$_2$, and Q$_3$ can be selected, can be further independently chosen from a group represented by one of the following formulas XIIIA and XIIIB, -M(T)$_{(t-1)}$    XIIIA -M(OT)$_{(t-1)}$,    XIIIB With reference to Formulas XIIIA and XIIIB, M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M.

Liquid crystal mesogens from which each of Q$_1$, Q$_2$, and Q$_3$ can each be independently selected, include but are not limited to art-recognized liquid crystal mesogens. With some embodiments, the liquid crystal mesogens can be selected from those described in United States Patent Application Publication No. US 2009/0323011 A1, see paragraphs [0052] to [0095] and Table 1, the disclosure of which is incorporated herein by reference in their entirety.

With further reference to Formula XIII, the subscripts c, d, e, and f are each independently chosen from an integer ranging from 1 to 20, inclusive of the upper and lower limits (e.g., from 2 to 15, or from 3 to 10).

The S$_1$, S$_2$, S$_3$, S$_4$, and S$_5$ groups of Formula XIII are each independently chose from a spacer unit. The spacer unit can in each case be independently chosen from, —(CH$_2$)$_g$—, —(CF$_2$)$_h$—, —Si(CH$_2$)$_g$—, —(Si(CH$_3$)$_2$O)$_h$—, in which g is independently chosen for each occurrence from 1 to 20, and h is a whole number from 1 to 16 inclusive. Alternatively, or additionally, the spacer unit can be independently chosen from —N(Z)—, —C(Z)=C(Z)—, —C(Z)=N—, —C(Z')—

C(Z')—, or a single bond, in which Z is independently chosen for each occurrence from hydrogen, $C_1$-$C_{18}$ alkyl, $C_3$-$C_{10}$ cycloalkyl and aryl, and Z' is independently chosen for each occurrence from $C_1$-$C_{18}$ alkyl, $C_3$-$C_{10}$ cycloalkyl and aryl. Further alternatively, or additionally, the spacer unit can be independently chosen from —O—, —C(O)—, —C≡C—, —N=N—, —S—, —S(O)—, —S(O)(O)—, —(O)S(O)O—, —O(O)S(O)O—, or straight-chain or branched $C_1$-$C_{24}$ alkylene residue, said $C_1$-$C_{24}$ alkylene residue being unsubstituted, mono-substituted by cyano or halo, or poly-substituted by halo.

With further reference to Formula XIII: when two spacer units comprising heteroatoms are linked together, the spacer units are linked so that heteroatoms are not directly linked to each other; each bond between $S_1$ and Ring-A and $S_1$ and Ring-B is free of two heteroatoms linked together; and the bond between $S_5$ and P is free of two heteroatoms linked to each other.

The P group of Formula XIII is chosen from, hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_8$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, alkylamino, $C_1$-$C_{18}$)alkylamino, alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy ($C_1$-$C_{18}$)alkyl, polyethyleneoxy, polypropyleneoxy, ethylenyl, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof. The substituents of the groups from which P can be selected are independently chosen from $C_1$-$C_{18}$ alkyl, $C_1$-$C_{18}$ alkoxy, amino, $C_3$-$C_{10}$ cycloalkyl, $C_1$-$C_{18}$ alkyl ($C_1$-$C_{18}$)alkoxy, fluoro($C_1$-$C_{18}$)alkyl, cyano, cyano($C_1$-$C_{18}$) alkyl, cyano($C_1$-$C_{18}$)alkoxy or mixtures thereof. With some embodiment P can be a structure having from 2 to 4 reactive groups. With further embodiments, P can be an unsubstituted or substituted ring opening metathesis polymerization precursor.

With further reference to Formula XIII, subscripts d', e' and f' are each independently chosen from 0, 1, 2, 3, and 4, provided that the sum of d'+e'+f' is at least 1.

Ring-A and Ring-B of the lactone compounds represented by Formulas I and II, are in some embodiments, each independently selected from unsubstituted and substituted aryl groups, such as unsubstituted and substituted phenyl groups. In accordance with some embodiments, of the present invention, the lactone compound is selected from lactone compounds represented by at least one of the following Formula Ia and Formula IIa:

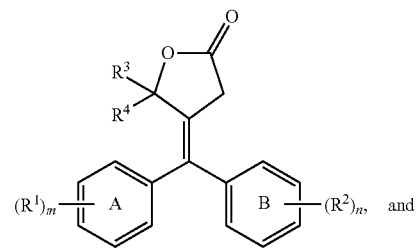

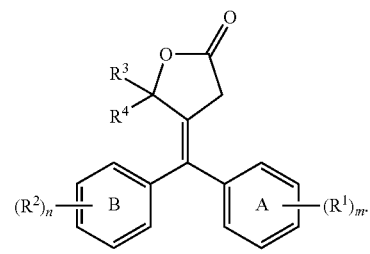

With Formulas Ia and IIa, m, n, $R^1$, $R^2$, $R^3$ and $R^4$ are each as described previously herein.

The lactone compound represented by at least one of Formula I and Formula II can, in some embodiments, be made or formed by a method that involves, reacting an acid ester represented by at least one of Formula VI and Formula VII with an metal hydride reducing agent that is defined herein to include an organo metal hydride reducing agent, or a nucleophile represented by at least one of Formula VIII and/or Formula IX, as described previously herein. The reaction by which the lactone compound is formed can be represented by the following Scheme-1.

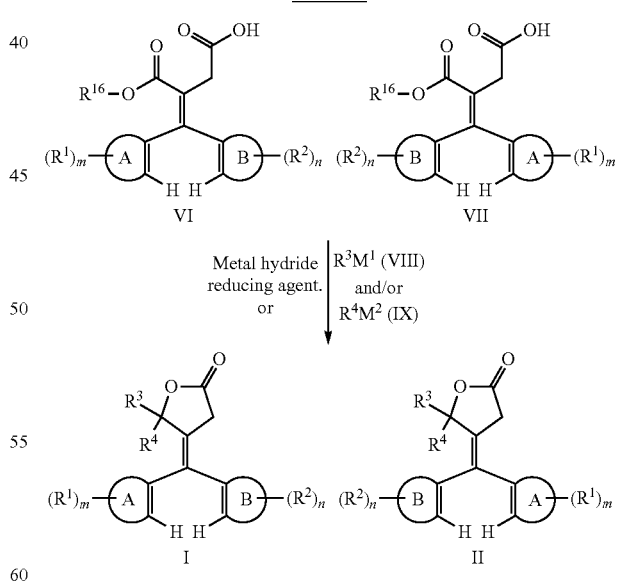

With the method of the present invention by which the lactone compound can be formed, for example as represented with reference to Scheme-1, the metal hydride reducing agent is typically used when $R^3$ and $R^4$ are each hydrogen. The metal hydride reducing agent can, in some embodiments, be selected from sodium borohydride and lithium aluminum hydride, or an organo metal hydride reducing agent. The organo metal hydride reducing agent can be one or more di($C_1$-$C_{20}$ alkyl) aluminum hydride reducing agents, such as one or more di($C_1$-$C_6$ alkyl) aluminum hydride reducing agents, e.g., diethyl aluminum hydride and diisobutyl aluminum hydride.

According to some embodiments of the present invention, $M^1$ and $M^2$ of Formulas VIII and IX also include a halogen, and can be represented by $(M^1X)^+$ and $(M^2X)^+$, in which X is a halogen. Each of $M^1$ and $M^2$ of Formulas VIII and IX can each be selected from $(MgX)^+$, in which X is selected from halogen, such as Cl, Br and I (e.g., $(MgCl)^+$, $(MgBr)^+$ and $(MgI)^+$).

With some embodiments of the present invention, the nucleophiles represented by Formulas VIII and IX are each Grignard reagents, and the reaction represented by Scheme-1 is a Grignard reaction, which is conducted under Grignard reaction conditions. The reaction represented by Scheme-1 is typically conducted in the presence of an appropriate solvent, such as tetrahydrofuran (THF), and under conditions of ambient pressure (e.g., approximately 1 atm), under an inert atmosphere (e.g., under a nitrogen sweep), such as from −30° C. to 60° C., or from −20° C. to 45° C., or from −10° C. to 30° C., and optionally with reflux.

The reaction of the acid ester represented by Formulas VI and/or VII with the nucleophile represented by Formulas VIII and/or IX can in some embodiments, be conducted in the presence of metal salts. Examples of metal salts that can be present include, but are not limited to, aluminum chloride ($AlCl_3$), tin chloride, zinc chloride, bismuth triflate, alkali metal halides, anhydrous alkaline metal halides, rate earth metal salts, e.g., lanthanide halides, such as lanthanum III chloride, and lanthanide triflate, and combinations thereof. Examples of alkali metal halides that can be present include, but are not limited to, sodium halides and/or potassium halides, such as sodium chloride (NaCl) and/or potassium chloride (KCl). Examples of alkaline metal halides that can be present include, but are not limited to, anhydrous calcium halides, anhydrous lithium halides and/or anhydrous magnesium halides, such as calcium chloride, lithium chloride and magnesium chloride. The metal salt is typically present in an amount of from 0.1 molar percent to 600 molar percent, or from 1.0 to 100 molar percent, or from 10 to 50 molar percent, based on 100 molar percent of the starting materials. The molar percent is defined herein as the percentage of the number of moles of the metal salt per liter of solute based on the total moles per liter of solute of the acid ester represented by Formulas VI and/or VII and the nucleophiles represented by Formulas VIII and IX in Scheme-1.

When the method of the present invention involves the formation of lactone compounds represented by Formulas Ia and/or IIa, the acid ester is represented by the following Formulas VIa and VIIa,

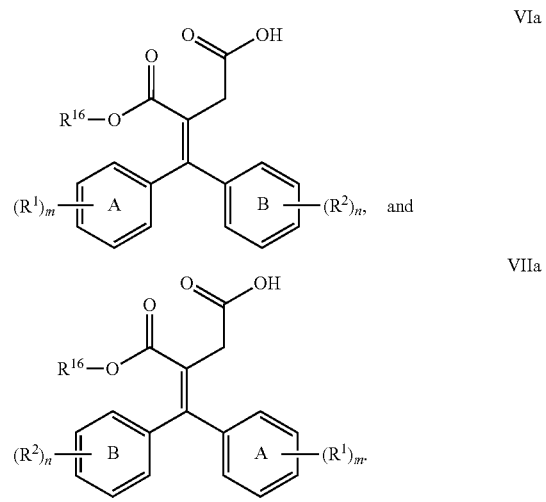

The acid esters represented by Formulas VI and VII can be prepared by appropriate methods. With some embodiments of the present invention, the acid esters represented by Formulas VI and VII are prepared by a reaction between a Ring-A Ring-B ketone and a succinic acid diester, as represented by the following Scheme-2.

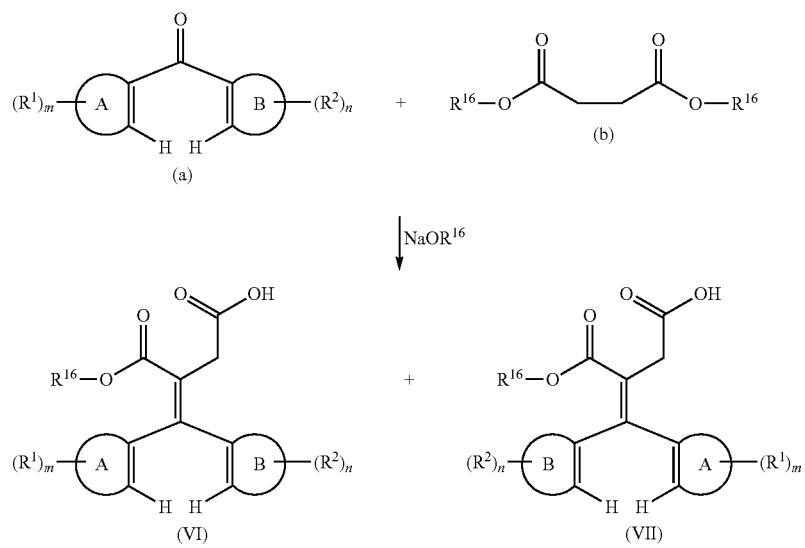

With reference to Scheme-2, the Ring-A Ring-B ketone (a) is reacted with a succinic acid diester (b), in which each $R^{16}$ is as described previously herein (e.g., each $R^{16}$ can be ethyl), in the presence of a strong base, such as an alkali metal alkoxide, such as $NaOR^{16}$ (e.g., sodium ethoxide). The reaction of Scheme-2 is conducted under appropriate conditions, such as under reflux at a temperature of the boiling point of the solvent, under an inert atmosphere, and in the presence of an appropriate solvent, such as tetrahydrofuran or toluene. The workup of the reaction is described in further detail in the Examples.

The present invention also provides a method of making an fused ring indenol compound represented by at least one of Formula III and Formula III-2, as described previously herein. As discussed previously herein, the method involves converting a lactone compound selected from lactone compounds represented by at least one of Formulas I and II, to an acid intermediate comprising an acid intermediate represented by at least one of Formula IV and Formula IV-2, each as described previously herein. The conversion of the lactone compound is typically conducted in the presence of one or more metal salt(s) which includes organo metal salts. With some embodiments, the metal salt is selected from:

(i) $Bi^{(3+)}(^-O-SO_2-R^{15})_3$, in which $R^{15}$ is selected from hydrocarbyl and halohydrocarbyl (e.g., a perhalohydrocarbyl); and/or (ii) $BiX_3$, where each X is selected independently from halogen (e.g., F, Cl and Br). The $R^{15}$ group of the organo metal salt is, with some embodiments, selected from a perhalohydrocarbyl group, such as a perhalo($C_1$-$C_{20}$)alkyl group, including, for example, perfluoro($C_1$-$C_6$)alkyl groups, such as $-CF_3$, $-C_2F_5$, and $-C_3F_7$. The metal salt typically is present in an amount, for example of from 0.001 molar percent to 50 molar percent or from 0.01 to 30 molar percent, or from 0.1 to 20 molar percent, based on 100 molar percent of the starting materials. In the conversion of lactones of Formula I and/or II to the acid intermediates of Formula IV and/or IV-2, molar percent is defined herein as the percentage of the number of moles of the metal salt per liter of solute based on the total moles per liter of solute of the lactones represented by Formulas I and/or II.

Conversion of the lactone compound represented by either Formula I or II to the acid intermediate, for example in the presence of a metal salt, results in formation of an acid intermediate represented by Formula IV and/or Formula IV-2. Depending on factors, including but not limited to, which lactone compounds are present, and the difference in the steric effect and/or the electron richness between Ring-A and Ring-B of the lactone compound(s) discussed herein below, the conversion can result in the formation of an acid intermediate composed more so of (e.g., substantially of) the acid intermediate represented by Formula IV or Formula IV-2, or a combination or mixture of acid intermediates represented by Formula IV and Formula IV-2.

It should be noted that conversion of a lactone compound represented by a mixture of Formula I and II, can result in the formation of an acid intermediate composed substantially, or exclusively, of the acid intermediate represented by Formula IV or Formula IV-2, or a mixture of both acid intermediates.

Also, conversion of lactone compounds represented by both Formulas I and II, can result in the formation of a combination or mixture of acid intermediates, as represented by the following Scheme-3.

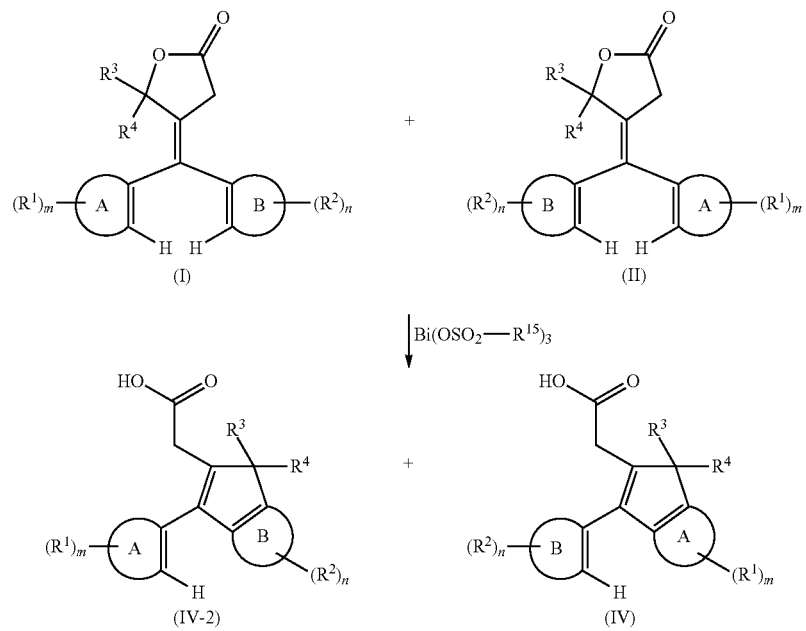

With reference to Scheme-3, a combination or mixture of acid intermediates IV and IV-2 are depicted as being formed. With some embodiments, the acid intermediates IV and IV-2 each can be isolated, and one or both of the isolated acid intermediates can be further converted to form the related indeno-fused ring compound. For example, further conversion of the acid intermediate represented by Formula IV, results in formation of the compound represented by Formula III; and, likewise, conversion of the acid intermediate represented by Formula IV-2 results in formation of a compound represented by Formula III-2.

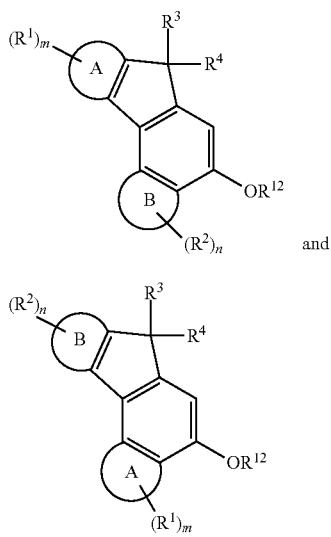

III

III-2

With some embodiments of the present invention, acid intermediates IV and IV-2 are not separated or isolated, and the subsequent conversion thereof results in the formation of a combination or mixture of compounds represented by Formulas III and III-2. The mixture of compounds represented by Formulas III and III-2 optionally can be separated or isolated from each other, for example, prior to further reactions performed there-with (e.g., the formation of an indeno-fused ring pyran compound).

In accordance with the present invention, conversion of a mixture of lactone compounds represented by Formulas I and II, can result in the formation of more of (i.e., a greater amount of) one of the acid intermediates than the other, e.g., more of the acid intermediate represented by Formula IV than of the acid intermediate represented by Formula IV-2. For example, the conversion can result in the formation of at least 50 mole percent, or at least 60 mole percent, or at least 70 mole percent, or at least 75 mole percent, or at least 80 mole percent of the acid intermediate represented by Formula IV, based on total moles of acid intermediate represented by Formula IV and acid intermediate represented by Formula IV-2. The acid intermediate represented by Formula IV can be formed in an amount of less than or equal to 100 mole percent, or less than or equal to 95 mole percent, or less than or equal to 90 mole percent, based on total moles of acid intermediate represented by Formula IV and acid intermediate represented by Formula IV-2. The amount of acid intermediate represented by Formula IV formed can range between any combination of these upper and lower limits, inclusive of the recited values, for example, from 50 to 100 mole percent, or from 60 to 95 mole percent, or from 70 to 90 mole percent of acid intermediate represented by Formula IV, based on total moles of acid intermediate represented by Formula IV and acid intermediate represented by Formula IV-2. In the same manner, the formation of more of the acid intermediate represented by Formula IV-2 than of the acid intermediate represented by Formula IV can occur.

Performing the conversion of the lactone compound comprising a mixture of lactone compounds represented by Formulas I and II, to result in the formation of a greater amount, of one of the two acid intermediates represented by Formula IV and Formula IV-2, can be achieved, for example, based on the difference in the steric effect and/or electron richness between Ring-A and Ring-B of the lactone compound(s). The selective conversion also can be performed in the presence of a metal salt selected, for example, from $Bi^{(3+)}(^{-}O-SO_2-R^{15})_3$, and/or $BiX_3$, each as described previously herein.

As used herein and in the claims, the term "steric effect" means and relates to the greater influence of the spatial configuration of one ring as compared to the other, e.g, Ring-A of the lactone compound as compared to Ring-B of the lactone compound, upon the rate, nature, and extent of the reaction. For example, the sizes and shapes of atoms and molecules, the geometry of bond angles and the presence of substituents influences the course of the reaction, as known to one skilled in the art. A lactone compound having a fluoro substituent at the 2 position of Ring-B, such as in Examples 3 and 6, appears to contribute to the steric hindrance for Ring-B making it less available for the reaction, resulting in the formation of more product of Formula IV.

As used herein and in the claims the term "electron richness" means and relates to the type, number and position of electron-donating groups and/or electron-withdrawing groups that are attached to Ring-A ($R^1$ group or groups) and Ring-B ($R^2$ group or groups) when Ring-A and Ring-B are the same. Electron richness can be measured by the Hammett Sigma value which refers to the relative strength of electron donating and withdrawing groups. The Hammett σ value is a relative measurement comparing the electronic influence of the substituent in the para ($\sigma_p$) or meta ($\sigma_m$) position of a phenyl ring to the electronic influence of a hydrogen substituted at the para or meta position. Typically for aromatic substituents in general, a negative Hammett σ value is indicative of a group or substituent having an electron-donating influence on a pi electron system (i.e., an electron-donating group) and a positive Hammett σ value is indicative of a group or substituent having an electron-withdrawing influence on a pi electron system (i.e., an electron-withdrawing group).

The effect of electron richness on the selectivity of the reaction, without intending to be bound by any theory, is believed to be as follows: there is less selectivity when there is less difference between the Hammett ($\sigma_p$) or ($\sigma_m$) values of either the electron withdrawing groups or electron donating groups on Ring-A and Ring-B of the lactone and there is more selectivity when there is a greater difference between these values. The selectivity of the reaction goes toward the Ring-A or Ring-B that is substituted with less electron withdrawing or more electron donating groups resulting in the corresponding acid intermediate of Formula IV or IV-2.

In Example 1, Ring-A and Ring-B are both benzene rings. Ring-A has a 3,5-dibromo substitution. The Hammett ($\sigma_p$) value of the 5-bromo is 0.23. Ring-B has a 4-trifluoromethyl substitutent. The Hammett ($\sigma_m$) value of the 4-trifluoromethyl is 0.43. No matter which isomer of Formula I or Formula II was used as the starting material, the formation of the product represented by Formula IV was preferred since Ring-B was less electron rich than was Ring-A. In Example 5, Ring-A and Ring-B are both benzene rings. Ring-A has a 4-methoxy substitutent. The Hammett ($\sigma_m$) value of the 4-methoxy is 0.12. Ring-B has a 3,5-dichloro substitution. The Hammett ($\sigma_p$) value of the 5-chloro is 0.23. The formation of the product represented by Formula IV was preferred since Ring-A was more electron rich than Ring-B.

When Ring-A and Ring-B are different, the "electron richness" does not only relate to the substituent attached to the ring, but also to the electronic properties of the ring. In Example 7, Ring-A was a thiophene ring while Ring-B was a benzene ring with a 4-fluoro substituent. The lone pair of electrons on the sulfur atom of the thiophene ring influenced the reaction to occur at Ring-A so formation of the product represented by Formula IV was preferred.

A tabular listing of $\sigma_p$ and $\sigma_m$ constants for a variety of substituents can be found in *Exploring QSAR, Hydrophobic, Electronic, and Steric Constants*, C. Hansch, A. Leo, and D. Hoekman, Eds., Published by The American Chemical Society, Washington, D.C., 1995, which disclosure is incorporated herein by reference. Examples of electron donors include, but are not limited to, amino, monoalkylamino, dialkylamino, morpholino, ethoxy, methoxy, p-aminophenyl, methyl, phenyl, and tolyl. Examples of electron-withdrawing groups include, but are not limited to, halogen, perfluoroalkyl and perfluoroalkoxy.

Additionally, conversion of the acid intermediate, for example represented by Formula IV or Formula IV-2, to the compound represented by Formula III or Formula III-2, where $R^{12}$ is hydrogen, can be conducted in two steps. Initially an ester intermediate represented by Formula V or Formula V-2 is formed, which is then reacted with a protonic acid so as to form the corresponding compound represented by Formula III or Formula III-2 in which $R^{12}$ is hydrogen, as represented by the following Scheme-4 and Scheme-4-2.

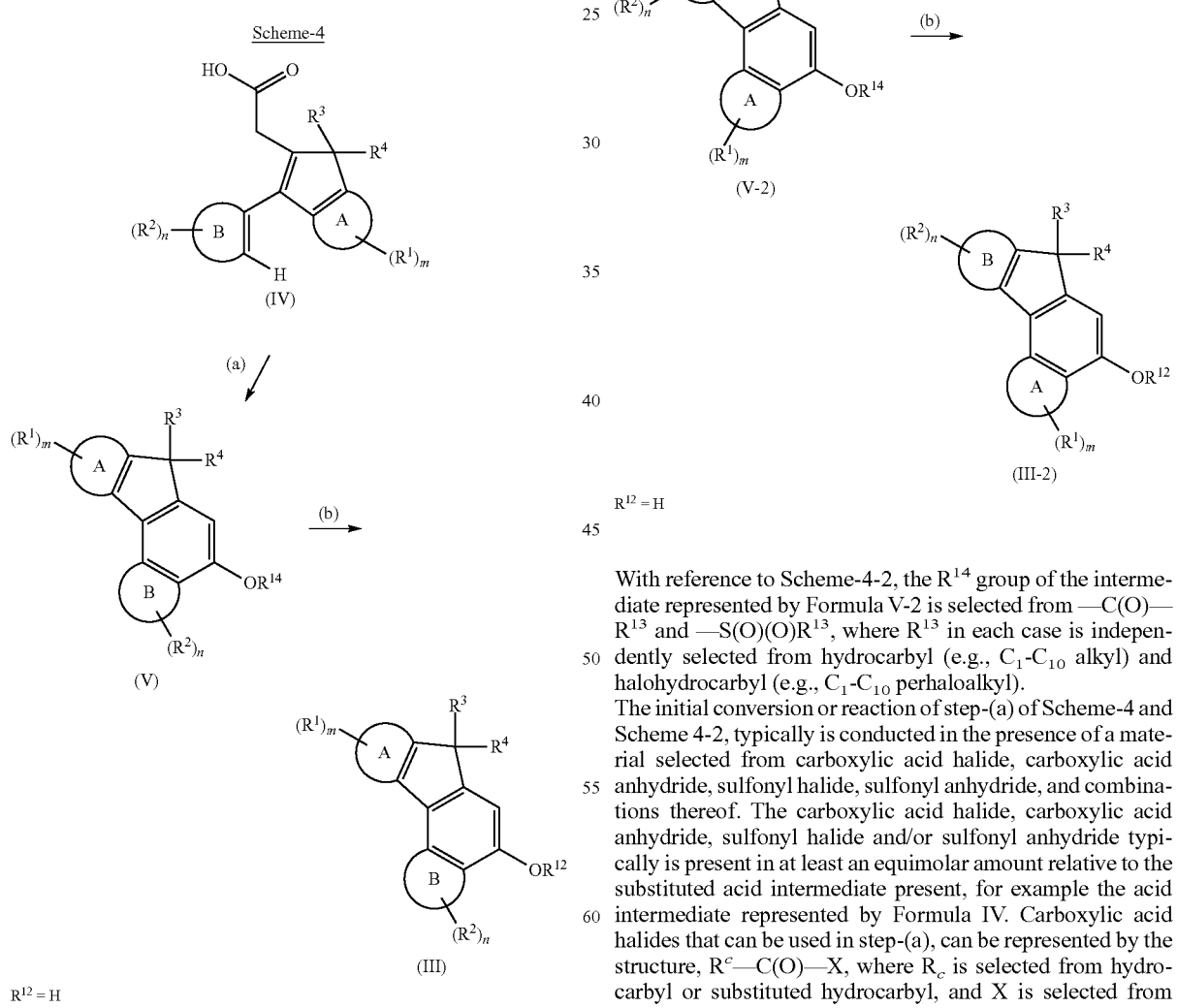

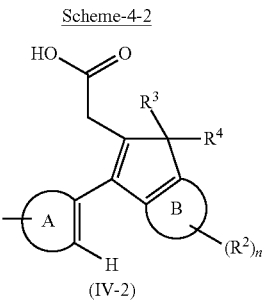

With reference to Scheme-4, the $R^{14}$ group of the indeno-fused ring ester intermediate represented by Formula V is selected from —C(O)—$R^{13}$ and —S(O)(O)$R^{13}$, where $R^{13}$ in each case is independently selected from hydrocarbyl (e.g., $C_1$-$C_{10}$ alkyl) and halohydrocarbyl (e.g., $C_1$-$C_{10}$ perhaloalkyl).

With reference to Scheme-4-2, the $R^{14}$ group of the intermediate represented by Formula V-2 is selected from —C(O)—$R^{13}$ and —S(O)(O)$R^{13}$, where $R^{13}$ in each case is independently selected from hydrocarbyl (e.g., $C_1$-$C_{10}$ alkyl) and halohydrocarbyl (e.g., $C_1$-$C_{10}$ perhaloalkyl).

The initial conversion or reaction of step-(a) of Scheme-4 and Scheme 4-2, typically is conducted in the presence of a material selected from carboxylic acid halide, carboxylic acid anhydride, sulfonyl halide, sulfonyl anhydride, and combinations thereof. The carboxylic acid halide, carboxylic acid anhydride, sulfonyl halide and/or sulfonyl anhydride typically is present in at least an equimolar amount relative to the substituted acid intermediate present, for example the acid intermediate represented by Formula IV. Carboxylic acid halides that can be used in step-(a), can be represented by the structure, $R^c$—C(O)—X, where $R_c$ is selected from hydrocarbyl or substituted hydrocarbyl, and X is selected from halogen (e.g., Cl). Sulfonyl halides that can be used in step-(a), can be represented by the formula, $R^d$—S(O)(O)—X, where $R^d$ is selected from hydrocarbyl or substituted hydrocarbyl, and X is selected from halogen (e.g., Cl). Carboxylic acid anhydrides that can be used in step-(a), can be represented by the formula, $R^e$—C(O)—O—C(O)—$R^f$, where $R^e$ and $R^f$ are each independently selected from hydrogen, hydrocarbyl, and substituted hydrocarbyl (e.g., halohydrocarbyl, such as $C_1$-$C_{10}$ perhaloalkyl, e.g., —$CF_3$). Sulfonyl anhydrides that can be used in step-(a), can be represented by the formulas $R^g$—S($O_2$)—O—S($O_2$)—$R^h$, where $R^g$ and $R^h$ are each independently selected from hydrocarbyl or substituted hydrocarbyl.

The intermediates represented by Formula V and Formula V-2 are converted to the corresponding compounds represented by Formula III and Formula III-2 (in which $R^{12}$ is hydrogen) in step-(b) of Scheme-4 and Scheme 4-2, respectively, by hydrolysis in the presence of a protonic acid or base. The protonic acid can be selected from hydrogen halides (HX, where X is halogen) such as HCl, sulfonic acids, phosphoric acids, and/or carboxylic acids. Examples of sulfonic acids include, but are not limited to para-toluene sulfonic acid and dodecyl benzene sulfonic acid. Examples of phosphoric acids include, but are not limited to phosphoric acid. Examples of carboxylic acids include, but are not limited to oxalic acid and acetic acid The base can be selected from sodium hydroxide and potassium hydroxide.

The protonic acid or base is typically present in an excess amount relative to the amount of intermediate represented by, for example, Formula V. For example the conversion of step-(b) can be conducted in the presence of concentrated hydrogen halide acid, such as concentrated HCl, a base, such as sodium hydroxide. The conversion of step-(b) is typically conducted in the presence of a solvent (e.g., methanol or methanol/water mixture), under reflux conditions, for example at a temperature from 20° C. to the reflux temperature of the solvent or from 25° C. to 90° C., or from 30° C. to 55° C., under conditions of ambient pressure (e.g., approximately 1 atm), and under an inert atmosphere, such as a nitrogen sweep.

Conversion of the acid intermediate, for example represented by Formula IV, to the compound represented by Formula III (in which $R^{12}$ is hydrogen) can, be conducted in substantially a single step, in the presence of a protonic acid. The protonic acid can be selected from carboxylic acids, sulfonic acids, phosphoric acids, which can each be selected from those classes and examples as described previously herein.

With the method of forming the compound represented by Formula III and Formula III-2, with the compounds and intermediates used and/or formed therewith, for example of the lactone compounds represented by Formulas I and II, and the acid intermediates represented by Formulas IV and IV-2, the various groups and subscripts associated therewith, such as n, m, $R^1$, $R^2$, $R^3$ and $R^4$ are each as described previously herein. With some embodiments, for example, $R^1$ for each m, and $R^2$ for each n, in each case are independently selected from $C_1$-$C_6$ alkyl, $C_3$-$C_7$ cycloalkyl, $C_1$-$C_8$ haloalkyl, fluoro, iodo, bromo, chloro, and —O—$R_{10}$'. With further embodiments, $R^3$ and $R^4$ are each independently selected from hydrogen, $C_1$-$C_8$ alkyl, $C_1$-$C_8$ haloalkyl, and $C_3$-$C_7$ cycloalkyl, or $R^3$ and $R^4$ together form a spiro substituent selected from a substituted or unsubstituted spiro-carbocyclic ring containing 3 to 6 carbon atoms.

With the method of forming the compounds represented by Formula III and Formula III-2 according to some embodiments of the present invention, Ring-A and Ring-B can each be phenyl rings. For example, the compound represented by Formula III, can be represented by the following Formula IIIa, and the compound represented by Formula III-2 can be represented by the following Formula III-2a,

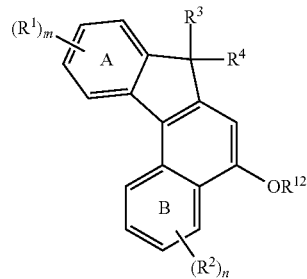

IIIa

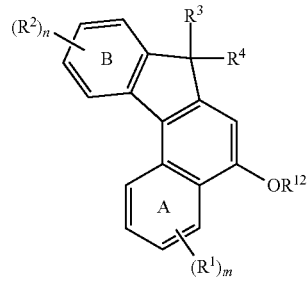

III-2a

With embodiments according to the present invention in which the compound is represented by Formula IIIa and/or Formula III-2a, the lactone compound is represented by Formulas Ia and IIa, as described previously herein, and the acid intermediate can be represented by the following Formula IVa and Formula IV-2a,

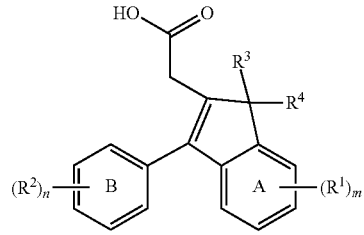

IVa

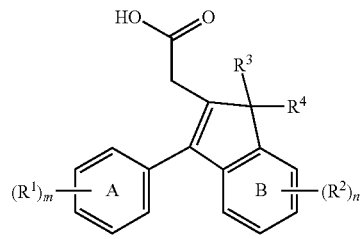

IV-2a

The present invention further provides a method of forming a fused ring indenopyran compound represented by Formula X and Formula X-2, as described previously herein. The method involves converting a lactone compound selected from lactone compounds represented by Formulas I and/or II, to an acid intermediate comprising an acid intermediate represented by Formula IV and Formula IV-2, in accordance with one or more of the embodiments as described previously herein. The acid intermediate represented by Formula IV and Formula IV-2 is converted to an fused ring indenol compound represented by Formula III and Formula III-2, in accordance with one or more of the embodiments as described previously herein. The fused ring indenol compound represented by Formula III, is then reacted with a propargyl alcohol represented by Formula XI, as described previously herein. Such a reaction is represented by the following Scheme-5.

Scheme-5

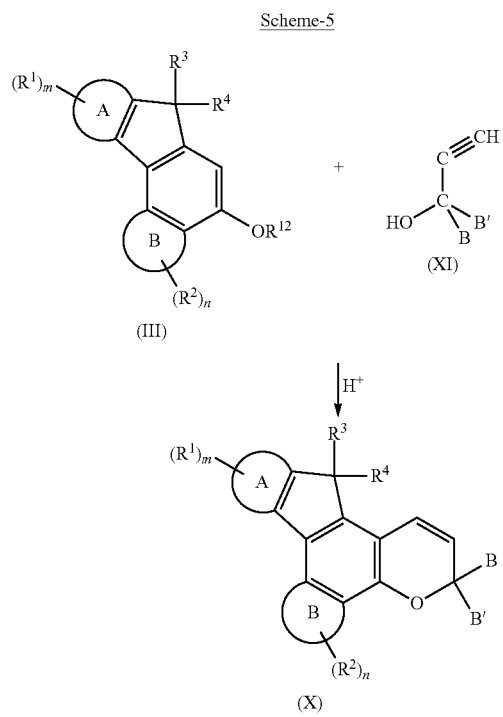

With reference to Scheme-5, the compound represented by Formula III is reacted or coupled with the propargyl alcohol represented by Formula XI in the presence of a catalytic amount of a protonic acid, such as dodecyl benzene sulfonic acid (DBSA) or para-toluene sulfonic acid (pTSA), in a suitable solvent, such as a haloalkyl (e.g., trichloromethane), under an inert atmosphere (e.g., a nitrogen sweep), and at a temperature range from 0° C. to the boiling point of the solvent, for example, from 0° C. to 55° C., or from 10° C. to 45° C., or from 20° C. to 25° C.

Similarly reaction of the compound represented by Formula III-2 with propargyl alcohol (XI) results in the formation of a fused ring indenopyran compound represented by the following Formula X-2,

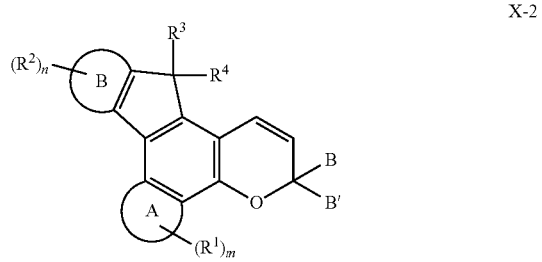

The various subscripts and groups, such as m, n, $R^1$, $R^2$, $R^3$, $R^4$, B and B' associated with Formulas III, XI, X and X-2 are as described previously herein. The B and B' groups, for example of Formulas X, X-2 and XI, are described in further detail as follows. More particularly, B and B' can each independently be selected from: an aryl group that is mono-substituted with a reactive substituent or a compatiblizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl. The phenyl, aryl, 9-julolindinyl, or heteroaromatic substituents are selected from: a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl.

The phenyl, aryl and heteroaromatic substituents (i.e., the substituents of the substituted phenyl, aryl and heteroaromatic groups) of the B and B' groups can each be independently selected from: hydroxyl, a group —C(=O)$R_{21}$, wherein $R_{21}$ is —O$R_{22}$, —N($R_{23}$)$R_{24}$, piperidino, or morpholino, wherein $R_{22}$ is allyl, $C_1$-$C_{20}$ alkyl, phenyl, mono($C_1$-$C_{20}$)alkyl substituted phenyl, mono($C_1$-$C_{20}$)alkoxy substituted phenyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and said halo substituent is chloro, iodo, bromo or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_3$-$C_{10}$ cycloalkylaryl, $C_3$-$C_{10}$ cycloalkyl, $C_3$-$C_{10}$ cycloalkyloxy, $C_3$-$C_{10}$ cycloalkyloxy($C_1$-$C_{20}$)alkyl, $C_3$-$C_{10}$ cycloalkyloxy($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di($C_1$-$C_{20}$)alkylaryl($C_1$-$C_{20}$)alkyl, mono- or di-($C_1$-$C_{20}$)alkoxyaryl($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$)alkoxy, amino, mono- or di-($C_1$-$C_{20}$)alkylamino, diarylamino, piperazino, N—($C_1$-$C_{20}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen.

The phenyl, aryl and heteroaromatic substituents (i.e., the substituents of the substituted phenyl, aryl and heteroaromatic groups) of the B and B' groups can, in some embodiments, each be independently and more particularly selected from: hydroxyl, a group —C(=O)$R_{21}$, wherein $R_{21}$ is —O$R_{22}$, —N($R_{23}$)$R_{24}$, piperidino, or morpholino, wherein $R_{22}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, $R_{23}$ and $R_{24}$ are each independently $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy, and said halo substituent is chloro, iodo, bromo or fluoro, aryl, mono($C_1$-$C_{12}$)alkoxyaryl, di($C_1$-$C_{12}$)alkoxyaryl, mono($C_1$-$C_{12}$)alkylaryl, di($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)

alkoxyaryl($C_1$-$C_{12}$)alkoxy, amino, mono- or di-($C_1$-$C_{12}$) alkylamino, diarylamino, piperazino, N—($C_1$-$C_{12}$) alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, alkoxy, mono($C_1$-$C_{12}$)alkoxy($C_1$-$C_{12}$) alkyl, acryloxy, methacryloxy, or halogen.

The B and B' groups can also each independently be an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{20}$ alkyl (e.g., $C_1$-$C_{12}$ alkyl), $C_1$-$C_{20}$ alkoxy (e.g., $C_1$-$C_{12}$ alkoxy), phenyl, or halogen.

In addition, the B and B' groups can each be independently selected from a group represented by the following general Formulas XIVA or XIVB,

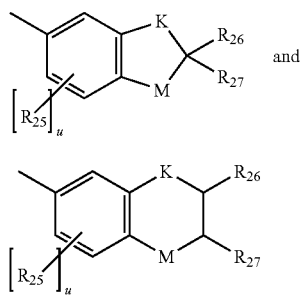

XIVA and

XIVB

Independently with each of general formulas XIVA and XIVB, K is —$CH_2$— or —O—, and M is —O— or substituted nitrogen, provided that when M is substituted nitrogen, K is —$CH_2$—, the substituted nitrogen substituents being hydrogen, $C_1$-$C_{20}$ alkyl, or $C_1$-$C_{20}$ acyl, each $R_{25}$ being independently chosen for each occurrence from $C_1$-$C_{20}$ alkyl, $C_1$-$C_{20}$ alkoxy, hydroxy, and halogen, $R_{26}$ and $R_{27}$ each being independently hydrogen or $C_1$-$C_{20}$ alkyl, and u is an integer ranging from 0 to 2.

Each B and B' group can independently be a group represented by the following general Formula XV,

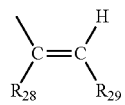

XV

With the group represented by general Formula XV, $R_{28}$ is hydrogen or $C_1$-$C_{12}$ alkyl, and $R_{29}$ is an unsubstituted, mono- or di-substituted group chosen from naphthyl, phenyl, furanyl, and thienyl. The substitutents of the mono- or di-substituted naphthyls, phenyls, furanyls, and thienyls, are in each case independently selected from $C_1$-$C_{12}$ alkyl, $C_1$-$C_{12}$ alkoxy, or halogen.

The B and B' groups can together form a member selected from, a fluoren-9-ylidene, a mono-substituted fluoren-9-ylidene, or a di-substituted fluoren-9-ylidene. The substituents of the mono-substituted fluoren-9-ylidene, and the di-substituted fluoren-9-ylidene can in each case be independently selected from $C_1$-$C_{20}$ alkyl (e.g., $C_1$-$C_{12}$ alkyl), $C_1$-$C_{20}$ alkoxy (e.g. $C_1$-$C_{12}$ alkoxy), or halogen.

With some embodiments of the present invention, and with further reference to the indeno-fused ring pyran represented by Formula X: $R^1$ for each m, and $R^2$ for each n, are in each case independently selected from $C_1$-$C_6$ alkyl, $C_3$-$C_7$ cycloalkyl, $C_1$-$C_8$ haloalkyl, fluoro, chloro, iodo, bromo and —O—$R_{10}$'; $R^3$ and $R^4$ are each independently selected from hydrogen, $C_1$-$C_8$ alkyl, $C_1$-$C_8$ haloalkyl, and $C_3$-$C_7$ cycloalkyl, or together form a spiro substituent selected from a substituted or unsubstituted spiro-carbocyclic ring containing 3 to 6 carbon atoms; and B and B' are each independently selected from aryl substituted with $C_1$-$C_6$ alkoxy, and aryl substituted with morpholino.

Ring-A and Ring-B can each be a phenyl ring, with some embodiments of the present invention, in which case the fused ring indenopyran represented by Formula X, can be represented by the following Formula Xa, and the fused ring indenopyran represented by Formula X-2, can be represented by the following Formula X-2a:

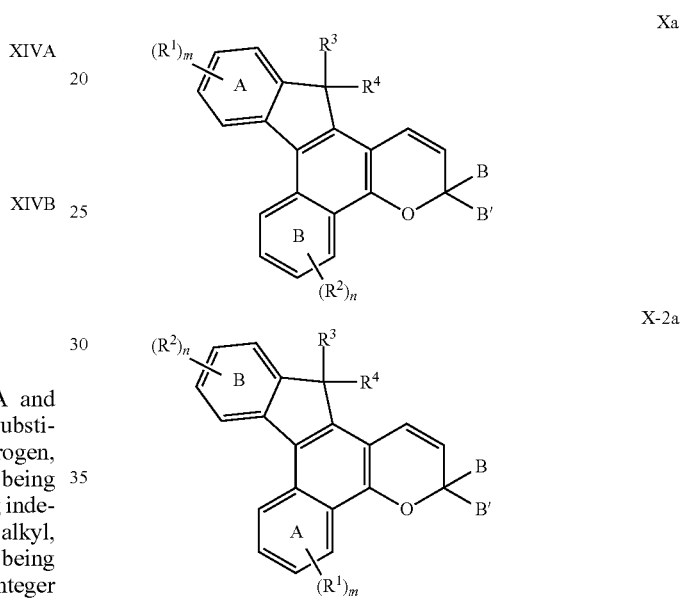

With some embodiments of the present invention, B and B' can each be independently selected from polyalkoxy, and polyalkoxy having a polymerizable group. The polyalkoxy, and polyalkoxy having a polymerizable group from which B and B' can each be independently selected can be represented by the following Formulas XXV and XXVI.

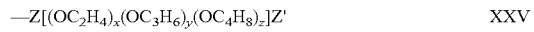

—Z[($OC_2H_4$)$_x$($OC_3H_6$)$_y$($OC_4H_8$)$_z$]Z'  XXV

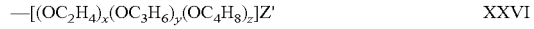

—[($OC_2H_4$)$_x$($OC_3H_6$)$_y$($OC_4H_8$)$_z$]Z'  XXVI

With Formulas XXV and XXVI, —Z is chosen from —C(O)— or —$CH_2$—, Z' is chosen from $C_1$-$C_3$ alkoxy or a polymerizable group. As used herein and in the claims, the term "polymerizable group" means any functional group capable of participating in a polymerization reaction.

With some embodiments, polymerization of the polymerizable indeno-fused naphthopyrans can occur by mechanisms described with regard to the definition of "polymerization" in *Hawley's Condensed Chemical Dictionary*, Thirteenth Edition, 1997, John Wiley & Sons, pages 901-902. Those mechanisms include: by "addition," in which free radicals are the initiating agents that react with the ethylenically unsaturated double bond of the monomer by adding to it on one side at the same time producing a new free electron on the other side; by "condensation," involving the splitting out of a component, such as water molecules, by two reacting monomers; and by so-called "oxidative coupling."

Examples of polymerizable groups include, but are not limited to, hydroxy, thiol, isocyanate groups, oxirane groups (e.g., oxiranylmethyl), radically polymerizable ethylenically unsaturated groups, allyl groups, (meth)acryloxy, and 2-(methacryloxy)ethylcarbamyl. When there are 2 or more polymerizable groups on the naphthopyran, they can be the same or different.

With some embodiments and with further reference to Formulas XXV and XXVI: the group, —(OC$_2$H$_4$)$_x$—, can represent poly(ethylene oxide); the group —(OC$_3$H$_6$)$_y$—, can represent poly(propylene oxide); and the group —(OC$_4$H$_8$)$_z$—, can represent poly(butylene oxide). When used in combination, the poly(ethylene oxide), poly(propylene oxide) and poly(butylene oxide) groups of Formulas XXV and XXVI can be in a random or block order within the polyalkoxy moiety. The subscript letters x, y and z of Formulas XXV and XXVI are each independently a number between 0 and 50, and the sum of x, y and z is between 2 and 50. The sum of x, y and z can be any number that falls within the range of 2 to 50 (e.g., 2, 3, 4 . . . 50). This sum can also range from any lower number to any higher number within the range of 2 to 50 (e.g., 6 to 50, 31 to 50). The numbers for x, y, and z are average values and can be partial numbers (e.g., 9.5).

As previously discussed, some of the groups of the various compounds and intermediates described herein, such as each of the R$^1$, R$^2$, R$^3$, R$^4$, B and B' groups, can independently be selected from or include at least one of a reactive substituent and/or a compatiblizing substituent. If the various compounds and/or intermediates described previously herein, such as the indeno-fused ring compound represented by Formula III, and/or the indeno-fused ring pyran compound represented by Formula X, include multiple reactive substituents and/or multiple compatiblizing substituents, each reactive substituent and each compatiblizing substituent can be independently chosen.

The reactive substituent and the compatibilizing substituent can each independently be represented in each case by one of:

-A'-D-E-G-J (XVI);

-G-E-G-J (XIX);

-D-E-G-J (XXII);

-A'-D-J (XVII);

-D-G-J (XX);

-D-J (XXIII);

-A'-G-J (XVIII);

-G-J (XXI); and

-A'-J (XXIV).

With formulas (XVI) through (XXIV), non-limiting examples of groups that -A'- can represent according to various non-limiting embodiments disclosed herein include —O—, —C(=O)—, —CH$_2$—, —OC(=O)— and —NHC (=O)—, provided that if -A'- represents —O—, -A'- forms at least one bond with -J.

Non-limiting examples of groups that -D- can represent according to various non-limiting embodiments include a diamine residue or a derivative thereof, wherein a first amino nitrogen of said diamine residue can form a bond with -A'-, or a substituent or an available position on the compound (such as the indeno-fused naphthol or indeno-fused naphthopyran), and a second amino nitrogen of said diamine residue can form a bond with -E-, -G- or -J; and an amino alcohol residue or a derivative thereof, wherein an amino nitrogen of the amino alcohol residue can form a bond with -A'-, or a substituent or an available position on the compound (such as the indeno-fused naphthol or indeno-fused naphthopyran), and an alcohol oxygen of said amino alcohol residue can form a bond with -E-, -G- or -J. Alternatively, according to various non-limiting embodiments disclosed herein the amino nitrogen of said amino alcohol residue can form a bond with -E-, -G- or -J, and said alcohol oxygen of said amino alcohol residue can form a bond with -A'-, or a substituent or an available position on the compound (such as the indeno-fused ring compound or indeno-fused ring pyran compound).

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. Specific non-limiting examples diamine residues that can be used in conjunction with various non-limiting embodiments disclosed herein include the following:

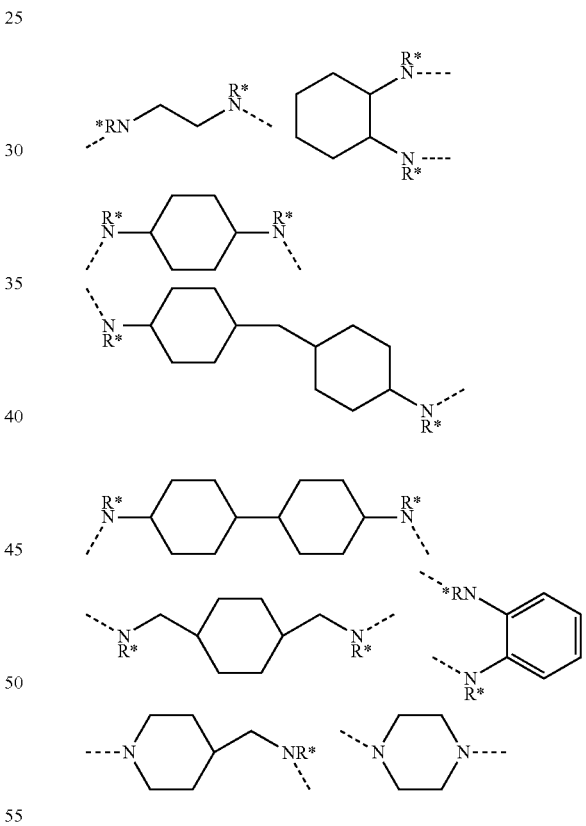

R* = H or alkyl

Non-limiting examples of suitable amino alcohol residues that -D- can represent include an aliphatic amino alcohol residue, a cyclo aliphatic amino alcohol residue, an azacyclo aliphatic alcohol residue, a diazacyclo aliphatic alcohol residue and an aromatic amino alcohol residue. Specific non-limiting examples amino alcohol residues that can be used in conjunction with various non-limiting embodiments disclosed herein include the following:

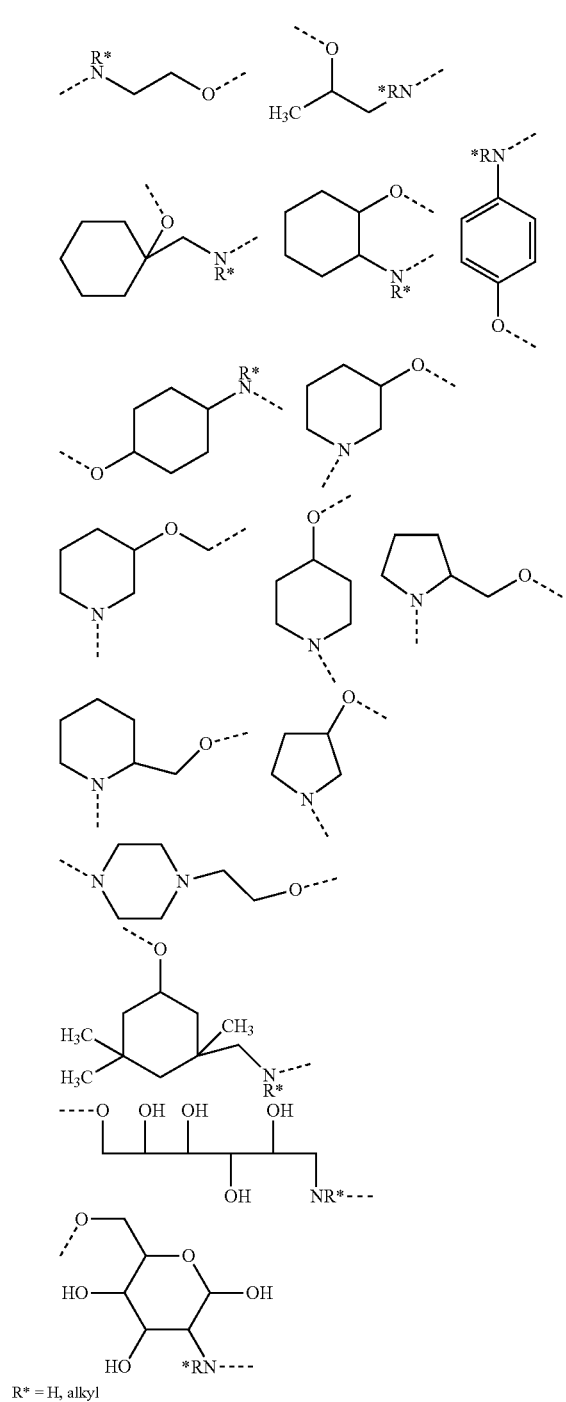

R* = H, alkyl

With continued reference to formulas (XVI) through (XXIV) above, according to various non-limiting embodiments disclosed herein, -E- can represent a dicarboxylic acid residue or a derivative thereof, wherein a first carbonyl group of said dicarboxylic acid residue can form a bond with -G- or -D-, and a second carbonyl group of said dicarboxylic acid residue can form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. Specific non-limiting examples of dicarboxylic acid residues that can be used in conjunction with various non-limiting embodiments disclosed herein include the following:

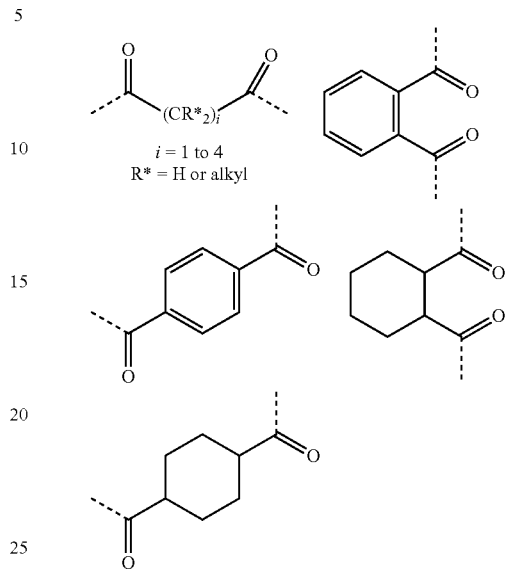

$i = 1$ to $4$
R* = H or alkyl

According to various non-limiting embodiments disclosed herein, -G- can represent a group $—[(OC_2H_4)_x(OC_3H_6)_y(OC_4H_8)_z]—O—$, wherein x, y and z are each independently chosen and range from 0 to 50, and a sum of x, y, and z ranges from 1 to 50; a polyol residue or a derivative thereof, wherein a first polyol oxygen of said polyol residue can form a bond with -A'-, -D-, -E-, or a substituent or an available position on the indeno-fused naphthopyran, and a second polyol oxygen of said polyol can form a bond with -E- or -J; or a combination thereof, wherein the first polyol oxygen of the polyol residue forms a bond with a group $—[(OC_2H_4)_x(OC_3H_6)_y(OC_4H_8)_z]—$ (i.e., to form the group $—[(OC_2H_4)_x(OC_3H_e)_y(OC_4H_8)_z]—O—$), and the second polyol oxygen forms a bond with -E- or -J. Non-limiting examples of suitable polyol residues that -G- can represent include an aliphatic polyol residue, a cyclo aliphatic polyol residue and an aromatic polyol residue.

More particular, illustrative and non-limiting examples of polyols from which the polyol residues that -G- can represent can be formed according to various non-limiting embodiments disclosed herein include: (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XVI) through (XXIV), according to various non-limiting embodiments disclosed herein, -J can represent a group —K, wherein —K represents a group such as, but not limited to, —$CH_2COOH$, —$CH(CH_3)COOH$, —$C(O)(CH_2)_w COOH$, —$C_6H_4SO_3H$, —$C_5H_{10}SO_3H$, —$C_4H_8SO_3H$, —$C_3H_6SO_3H$, —$C_2H_4SO_3H$ and —$SO_3H$, wherein "w" ranges from 1 to 18. According to other non-limiting embodiments -J can represent hydrogen that forms a bond with an oxygen or a nitrogen of linking group to form a reactive moiety such as —OH or —NH. For example, according to various non-limiting embodiments disclosed herein, -J can represent hydrogen, provided that if -J represents hydrogen, -J is bonded to an oxygen of -D- or -G-, or a nitrogen of -D-.

According to still further non-limiting embodiments, -J can represent a group -L or residue thereof, wherein -L can represent a reactive moiety. For example, according to various non-limiting embodiments disclosed herein -L can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

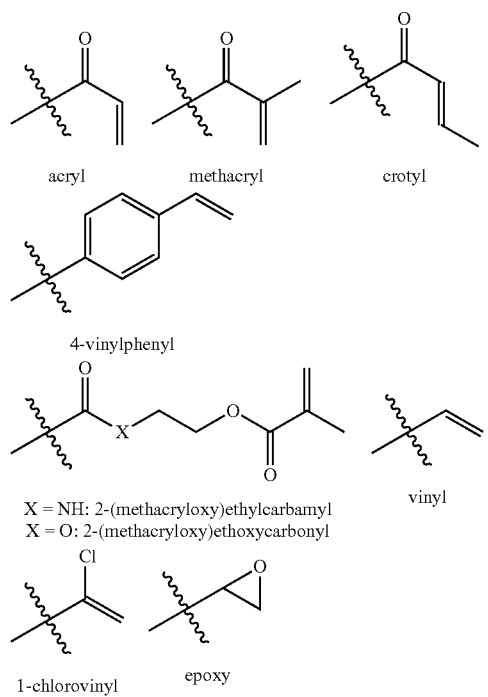

As previously discussed, -G- can represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol can be represented by $q$-$(OH)_a$ and the residue of the polyol can be represented by the formula —O-$q$-$(OH)_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatiblizing substituent comprises the group -G-J, if -G- represents a polyol residue and -J represents a group —K that contains a carboxyl terminating group, -G-J can be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J can be produced by acidic condensation of one or more of the polyol hydroxyl groups with $HOC_6H_4SO_3H$; $HOC_5H_{10}SO_3H$; $HOC_4H_8SO_3H$; $HOC_3H_6SO_3H$; $HOC_2H_4SO_3H$; or $H_2SO_4$, respectively. Further, although not limiting herein, if -G- represents a polyol residue and -J represents a group -L chosen from acryl, methacryl, 2-(methacryloxy)ethylcarbamyl and epoxy, -L can be added by condensation of the polyol residue with acryloyl chloride, methacryloyl chloride, 2-isocyanatoethyl methacrylate or epichlorohydrin, respectively.

The indeno-fused ring pyran compounds, such as indeno-fused naphthopyrans, prepared by the method of the present invention, can be used to render compositions and/or articles photochromic. Examples of articles that can be rendered photochromic by the indeno-fused ring pyran compounds of the present invention include, but are not limited to, optical elements, displays, windows (or transparencies), mirrors, and components or elements of liquid crystal cells. As used herein the term "optical" means pertaining to or associated with light and/or vision. Examples of optical elements that can be rendered photochromic include, without limitation, ophthalmic elements, display elements, windows, mirrors, and liquid crystal cell elements. As used herein the term "ophthalmic" means pertaining to or associated with the eye and vision. Non-limiting examples of ophthalmic elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, magnifying lenses, protective lenses, visors, goggles, as well as, lenses for optical instruments (for example, cameras and telescopes). As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation there-through. Non-limiting examples of windows include automotive and aircraft transparencies, windshields, filters, shutters, and optical switches. As used herein the term "mirror" means a surface that specularly reflects a large fraction of incident light. As used herein the term "liquid crystal cell" refers to a structure containing a liquid crystal material that is capable of being ordered. One non-limiting example of a liquid crystal cell element is a liquid crystal display.

Articles can be rendered photochromic with the indeno-fused ring pyran compounds of the present invention by methods including, but not limited to, imbibition methods, cast-in-place methods, coating methods, in-mold coating methods, over-mold methods, and lamination methods. With imbibition methods, the indeno-fused ring pyran compound is typically diffused into a polymeric material of a previously formed or fabricated article, such as a substrate or previously applied coating or film. Imbibition can be performed by immersing the polymeric material of a previously formed or fabricated article in a solution containing the indeno-fused ring pyran compound, with or without heating. Thereafter, although not required, the indeno-fused ring pyran compound can be bonded with the polymeric material (e.g., of the substrate or coating).

With cast-in-place methods, the indeno-fused ring pyran compound can be mixed with: a polymer and/or oligomer composition in solution or melt form; or monomer composition in liquid form, so as to form a castable photochromic composition. The castable photochromic composition is then typically introduced into the cavity of a mold (e.g., a lens mold). The castable photochromic composition is then set (e.g., cured) within the mold so as to form a photochromic article.

With articles that include a substrate, the fused ring indenopyran compounds of the present invention can be connected to at least a portion of the substrate as part of a coating that is connected to at least a portion of the substrate. The substrate can be a polymeric substrate or an inorganic substrate (such as, but not limited to, a glass substrate). The fused ring indenopyran compound of the present invention can be incorporated into at least a portion of a coating composition prior to application of the coating composition to the substrate. Alternatively, a coating composition can be applied to the substrate, at least partially set, and thereafter the fused ring indenopyran compound of the present invention can be imbibed into at least a portion of the coating. As used herein, the terms "set" and "setting" include, without limitation, curing, polymerizing, cross-linking, cooling, and drying.

Photochromic articles can be prepared using the fused ring indenopyran compounds of the present invention by art-recognized in-mold coating (or in-mold casting) methods. With in-mold coating methods, a photochromic coating composition including the fused ring indenopyran compound of the present invention, which can be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic article is then removed from the mold. Non-limiting examples of powder coatings in which the indeno-fused ring pyran compounds according to various non-limiting embodiments disclosed herein can be employed are set forth in U.S. Pat. No. 6,068,797 at col. 7, line 50 to col. 19, line 42, which disclosure is hereby specifically incorporated by reference herein.

Photochromic articles prepared using the fused ring indenopyran compounds of the present invention can also be formed by art-recognized over-mold methods. Over-mold methods typically involve forming a substrate within a mold, and then forming an interior space between the substrate and an interior surface of the mold, into which a photochromic coating composition is then subsequently introduced (e.g., injected) and then set (e.g., cured). Alternatively, over-mold methods can involve introducing a previously formed substrate into a mold, such that an interior space is defined between the substrate and an interior mold surface, and thereafter a photochromic coating composition is introduced (e.g., injected) into the interior space.

Photochromic articles, prepared using the fused ring indenopyran compounds prepared by the methods of the present invention, can also be formed by art-recognized lamination methods. With lamination methods, a film comprising the fused ring indenopyran compounds of the present invention can be adhered or otherwise connect to a portion of the substrate, with or without an adhesive and/or the application of heat and pressure. Thereafter, if desired, a second substrate can be applied over the first substrate and the two substrates can be laminated together (e.g., by the application of heat and pressure) to form an element wherein the film comprising the fused ring indenopyran compound is interposed between the two substrates. Methods of forming films comprising a photochromic material can include for example and without limitation, combining a photochromic material with a polymeric solution or oligomeric solution or mixture, casting or extruding a film therefrom, and, if required, at least partially setting the film. Additionally or alternatively, a film can be formed (with or without a photochromic material) and imbibed with the photochromic material.

The fused ring indenopyran compounds prepared by the methods of the present invention, can be used alone or in combination with other photochromic materials. Classes of photochromic materials that can be used in combination (e.g., in mixture) with the fused ring indenopyran compounds of the present invention include, but are not limited to: spiro(indoline)naphthoxazines and spiro(indoline)benzoxazines, for example as described in U.S. Pat. Nos. 3,562,172, 3,578,602, 4,215,010, 4,342,668, 5,405,958, 4,637,698, 4,931,219, 4,816,584, 4,880,667, and 4,818,096; benzopyrans, for example as described in U.S. Pat. Nos. 3,567,605, 4,826,977, 5,066,818, 4,826,977, 5,066,818, 5,466,398, 5,384,077, 5,238,931, and 5,274,132; photochromic organo-metal dithizonates, such as, (arylazo)-thioformic arylhydrazidates, e.g., mercury dithizonates which are described in, for example, U.S. Pat. No. 3,361,706; and fulgides and fulgimides, e.g., the 3-furyl and 3-thienyl fulgides and fulgimides which are described in U.S. Pat. No. 4,931,220 at column 20, line 5 through column 21, line 38.

EXAMPLES

In Part 1 of the Examples, the synthesis procedures used to make the lactones of Examples 1-8, naphthol of Example 7B and photochromic materials of Examples 1A to 6A. Part 2 describes the photochromic performance testing and results for photochromic compounds of Examples 1A-6A.

Part 1: Synthesis of the Lactones of Examples 1-8, Naphthol of Example 7B and Photochromic Compounds of Examples 1A-6A Example 1

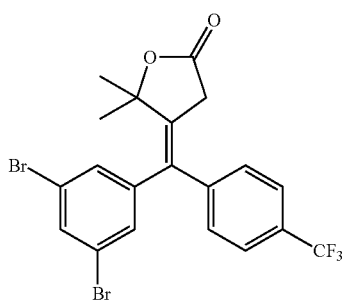 [SMILES: CC1(C)OC(=O)C/C1=C(\c1ccc(C(F)(F)F)cc1)c1cc(Br)cc(Br)c1]

Step 1

A 2 L flask with tribromobenzene (100 g) and a magnetic stir bar was dried in a vacuum oven at 80° C. for 4 hours. Dry THF (500 ml) was added. The resulting mixture was placed in an NaCl saturated ice bath. 3M isopropyl magnesium chloride (160 mL) was added drop wise to the solution at a rate so that the inside temperature was controlled to −20 to 0° C. The addition was finished in about 30 minutes to 1 hour. The mixture was stirred for half an hour at the same temperature and bis[2-(N,N-dimethylamino)ethyl]ether (61 g) was added slowly over a 5 minutes interval and a large amount of precipitate formed. The resulting mixture was stirred for 20 minutes and a mixture of 4-trifluoromethylbenzoyl chloride (73 g) and THF (100 mL) was added over a 5 minute interval. The resulting mixture was stirred overnight. Water (100 mL) was added slowly and the pH was adjusted to 2 with 3N HCl. The resulting organic layer was collected by a separatory funnel, washed with 5% NaOH/water and NaCl/water, dried and concentrated. To the recovered oil, methanol (300 mL) was added and the product crystallized. The product was collected by vacuum filtration. NMR showed that the obtained white crystals (87 g) have a structure consistent with 3,5-dibromo-4'-trifluoromethylbenzophenone.

Step 2

A mixture of the product of Step 1 (75 g), dimethyl succinic ester (32.2 g) and toluene (800 ml) were placed in a three neck 5 L flask equipped with a mechanical stir. Potassium t-butoxide (22.6 g) was added batch wise over a 30 minute interval. An exothermic reaction along with the formation of a large amount of precipitate was observed. After two hours, water (500 mL) was added. The pH of the mixture was adjusted to ~2 using 3 N HCl. After stirring at room temperature for 10 minutes, the resulting organic layer was collected, washed with NaCl/water, dried over $MgSO_4$. After concentration, hexanes were added and white crystals formed. The crystals were collected by vacuum filtration. NMR showed that the obtained product (62 grams) had a structure consistent with (E)-4-(3,5-dibromophenyl)-3-(methoxycarbonyl)-4-(4-(trifluoromethyl)phenyl)but-3-enoic acid. This step was repeated to produce more product for the next Step.

Step 3

Solid anhydrous lanthanum (III) chloride (100 g) was ground to a very fine powder and then mixed with lithium chloride (52 g) and dry THF (1 liter) in a 5 liter three-neck flask equipped with a mechanical stir and a dropping funnel. The mixture was refluxed for few hours until it dissolved. The product of Step 2 was dissolved in the mixture. The mixture was then cooled to −15° C. A solution of 3M methyl magnesium chloride (238 mL) was placed in the dropping funnel. The first 30% of the Grignard was added slowly to the mixture. Generation of gas bubbles and the rise of the mixture temperature were observed. After the temperature returned to −15° C., the remainder of the Grignard was added to the mixture over 2 minutes. After 30 minutes, water (1 L) was added slowly to the mixture and the pH was adjusted to acidic using acetic acid. The mixture turned clear with formation of two layers. The water layer was drained off. The recovered organic layer was washed with NaCl/water four times and then concentrated to dry. A light yellowish solid was recovered and dissolved in toluene. The solution was filtered using a silica gel plug column and the recovered clear solution was concentrated to dryness. White solid product was obtained and used in the next Step without further purification. A portion of the product was recrystallized from methanol and NMR analysis showed that the purified crystals had a structure consistent with (E)-(beta-((3,5-dibromophenyl)(4-(trifluoromethyl)phenyl)methylene))-gamma,gamma-dimethyl-gamma-butyrolactone. NMR also showed that the unpurified white solid product had a mixture of E/Z isomer of beta-((3,5-dibromophenyl)(4-(trifluoromethyl)phenyl)methylene)-gamma,gamma-dimethyl-gamma-butyrolactone.

Example 1A

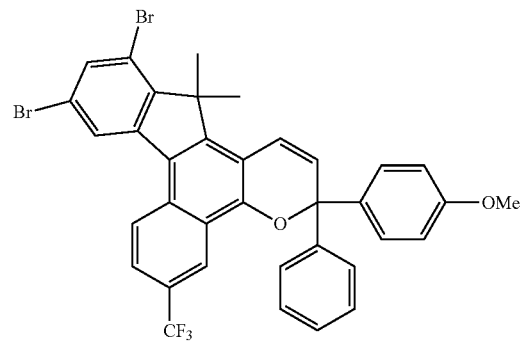 [SMILES: COc1ccc(C2(c3ccccc3)C=Cc3c4c(c5ccc(C(F)(F)F)cc5c3O2)-c2cc(Br)cc(Br)c2C4(C)C)cc1]

Step 1

A mixture of the product from Example 1, toluene (500 mL), bismuth triflate (20 g) and acetic acid (0.24 g) was stirred at reflux for 1 hour. After cooling back to room temperature, acetic anhydride (100 mL) was added. The mixture was heated to reflux again. After one hour, the mixture was cooled to room temperature and filtered through a silica gel plug column and eluted with toluene. The resulting clear solution was concentrated. Acetone (50 mL) was added and a slurry was obtained. To the slurry mixture, methanol (250 mL) was added and the mixture was cooled in an ice bath. White crystals were collected and dried to yield 58 g of product. NMR showed that the product had a structure consistent with 8,10-dibromo-7,7-dimethyl-3-(trifluoromethyl)-7H-benzo[c]fluoren-5-yl acetate.

Step 2

To a flask containing the product of Step 1 (2.42 g) 1 were added methanol (20 mL) and tetrahydrofuran (10 mL). Concentrated hydrochloric acid (1 mL) was added and the solution was heated to reflux for 4 h. The solvent was removed under vacuum and the residue was purified by passing through a plug of silica gel, using 4:1 hexane/ethyl acetate mixture as the eluent. Fractions containing the desired material were grouped and concentrated to provide a cream colored solid (1.63 g). NMR analysis of the cream colored solid indicated a structure that was consistent with 8,10-dibromo-7,7-dimethyl-3-(trifluoromethyl)-7H-benzo[c]fluoren-5-ol.

Step 3

To a dichloroethane solution (100 mL) of the product of Step 2 were added 1-(4-methoxyphenyl)-1-phenylprop-2-yn-1-ol (4 g) and p-toluenesulfonic acid (32 mg). The solution was heated to reflux for 2 h. The reaction mixture was concentrated under reduced pressure. The product was purified with silica gel plug column separation followed by recrystallization from acetone/methanol. The grey crystals were collected by vacuum filtration (7.6 g). NMR analysis of the product indicated a structure that was consistent with 3-(4-methoxyphenyl)-3-phenyl-10,12-dibromo-6-trifluoromethyl-13,13-dimethyl-3H,13H-indeno[2',3':3,4]naphtho[1,2-b]pyran.

Example 2

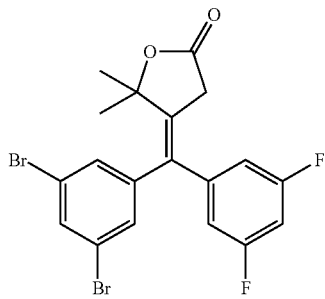 [SMILES: CC1(C)OC(=O)C/C1=C(\c1cc(F)cc(F)c1)c1cc(Br)cc(Br)c1]

Procedures from Step 1 to Step 3 of Example 1 were followed except that 3,5-difluorobenzoyl chloride was used in place of 4-trifluoromethylbenzoyl chloride. White solids were obtained as the product. NMR indicated that the product had a structure consistent with a mixture of E/Z isomer of beta-((3,5-dibromophenyl)(3,5-difluorophenyl)methylene)-gamma,gamma-dimethyl-gamma-butyrolactone.

Example 2A

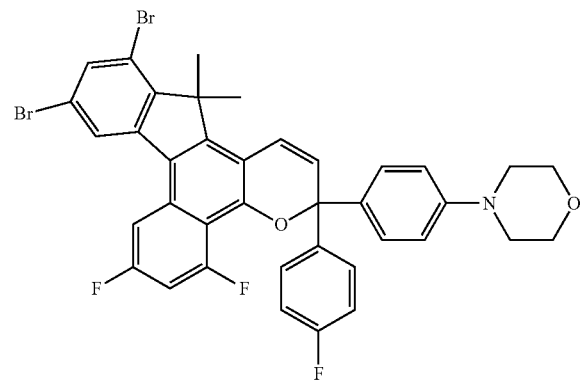 [SMILES: CC1(C)c2c(Br)cc(Br)cc2-c2c1c1c(c3c(F)cc(F)cc23)OC(c2ccc(F)cc2)(c2ccc(N3CCOCC3)cc2)C=C1]

The procedures from Step 1 to Step 3 of Example 1A were followed except that: in Step 1, the product of Example 2 was used in place of the product of Example 1; in Step 2, the desired product 8,10-dibromo-2,4-difluoro-7,7-dimethyl-7H-benzo[c]fluoren-5-ol was recrystallized out using ethyl acetate as solvent; in Step 3, 1-(4-fluorophenyl)-1-(4-(N-morpholino)phenyl)prop-2-yn-1-ol was used in place of 1-(4-methoxyphenyl)-1-phenylprop-2-yn-1-ol. NMR confirmed that the final product had a structure consistent with 3-(4-fluorophenyl)-3-(4-morpholinophenyl)-10,12-dibromo-5,7-difluoro-13,13-dimethyl-3H,13H-indeno[2',3':3,4]naphtho[1,2-b]pyran.

Example 3

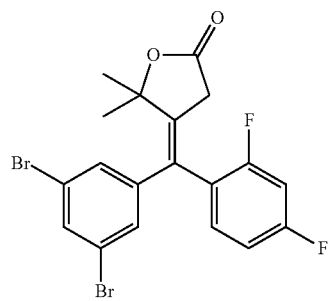 [SMILES: CC1(C)OC(=O)C/C1=C(/c1cc(Br)cc(Br)c1)c1ccc(F)cc1F]

Procedures from Step 1 to Step 3 of Example 1 were followed except that 2,4-difluorobenzoyl chloride was used in place of 4-trifluoromethylbenzoyl chloride in Step 1. White solids were obtained as the product. NMR indicated that the product had a structure consistent with a mixture of E/Z isomer of beta-((3,5-dibromophenyl)(2,4-difluorophenyl)methylene)-gamma,gamma-dimethyl-gamma-butyrolactone.

Example 3A

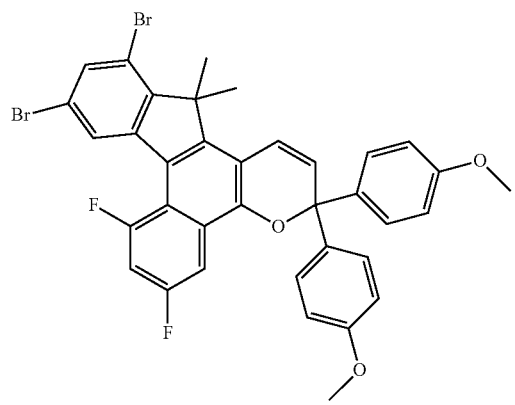 [SMILES: COc1ccc(C2(c3ccc(OC)cc3)C=Cc3c4c(c5c(F)cc(F)cc5c3O2)-c2cc(Br)cc(Br)c2C4(C)C)cc1]

The procedures from Step 1 to Step 3 of Example 1A were followed except that: in Step 1, the product of Example 3 was used in place of the product of Example 1; in Step 3, 1,1-bis(4-methoxyphenyl)prop-2-yn-1-ol was used in place of 1-(4-methoxyphenyl)-1-phenylprop-2-yn-1-ol. NMR analysis of the obtained off-white crystals indicated a structure that was consistent with 3,3-bis(4-methoxyphenyl)-10,12-dibromo-6,8-difluoro-13,13-dimethyl-3H,13H-indeno[2',3':3,4]naphtho[1,2-b]pyran.

Example 4

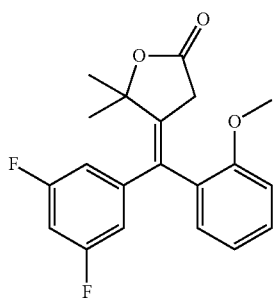 [SMILES: COc1ccccc1/C(=C1\CC(=O)OC1(C)C)c1cc(F)cc(F)c1]

Procedures from Step 1 to Step 3 of Example 1 were followed except that 3,5-difluorobromobenzene and 2-methoxybenzoyl chloride were used in place of tribromobenzene and 4-trifluoromethylbenzoyl chloride in Step 1 and product from Step 2 was purified by column separation. A clear oil was obtained as the product. NMR indicated that the product had a structure consistent with a mixture of E/Z isomer of beta-((3,5-difluorophenyl)(2-methoxyphenyl)methylene)-gamma,gamma-dimethyl-gamma-butyrolactone.

Example 4A

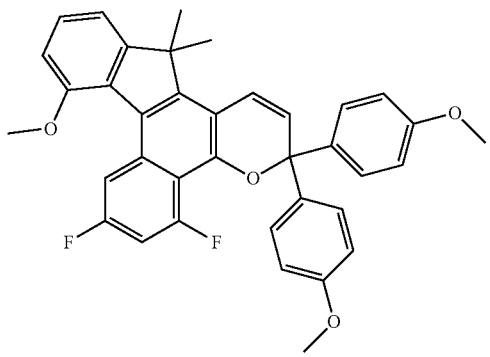

The procedures from Step 1 to Step 3 of Example 1A were followed except that: in Step 1, the product of Example 4 was used in place of the product of Example 1; also in Step 1 before the addition of acetic anhydride, the toluene solution was washed with water, dried over magnesium and filtered though CELITE® filter aid to remove bismuth triflate; in Step 3, 1,1-bis(4-methoxyphenyl)prop-2-yn-1-ol was used in place of 1-(4-methoxyphenyl)-1-phenylprop-2-yn-1-ol. NMR confirmed that the off-white crystalline product had a structure consistent with 3,3-bis(4-methoxyphenyl)-9-methoxy-5,7-difluoro-13,13-dimethyl-3H,13H-indeno[2',3':3,4]naphtho[1,2-b]pyran.

Example 5

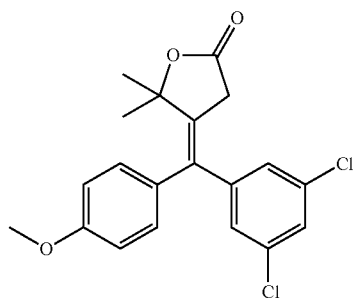 [SMILES: COc1ccc(/C(=C2/CC(=O)OC2(C)C)c2cc(Cl)cc(Cl)c2)cc1]

Procedures from Step 1 to Step 3 of Example 1 were followed except that 3,5-dichlorobromobenzene and 4-methoxybenzoyl chloride was used in place of tribromobenzene and 4-trifluoromethylbenzoyl chloride in Step 1. White solid was obtained as the product. NMR indicated that the product had a structure consistent with a mixture of E/Z isomer of beta-((3,5-dichlorophenyl)(4-methoxyphenyl)methylene)-gamma,gamma-dimethyl-gamma-butyrolactone.

Example 5A

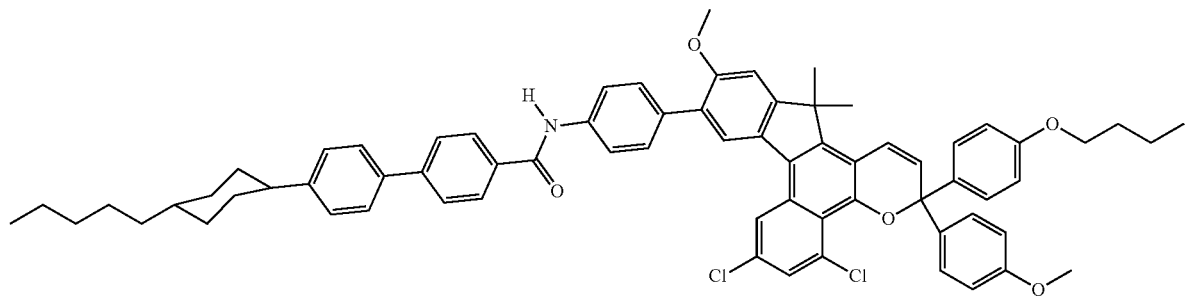 [SMILES: CCCCCC1CCC(c2ccc(-c3ccc(C(=O)Nc4ccc(-c5cc6c(cc5OC)C(C)(C)c5c7c(c8c(Cl)cc(Cl)cc8c5-6)OC(c5ccc(OC)cc5)(c5ccc(OCCCC)cc5)C=C7)cc4)cc3)cc2)CC1]

Step 1

The procedure from Step 1 of Example 1A was followed except that the product of Example 5 was used in place of the product of Example 1. An off-white solid was obtained as the product. NMR indicated that the product had a structure consistent with 2,4-dichloro-9-methoxy-7,7-dimethyl-7H-benzo[c]fluoren-5-yl acetate.

Step 2

A mixture of the product of Step 1 (5 g), N-bromosuccinimide (2.7 g) and DMF (100 mL) was stirred in a reaction flask and heated at 90° C. for two hours. The reaction mixture was poured into water (400 mL) and extracted with 1/1 ethyl acetate/THF (200 mL). The organic layer was collected, washed with sodium bisulfite aqueous solution three times, dried and concentrated. To the obtained crude product, methanol (100 mL) was added. After filtration, off white solid (4.4 g) was obtained as the product. NMR indicated that the product had a structure consistent with 10-bromo-2,4-dichloro-9-methoxy-7,7-dimethyl-7H-benzo[c]fluoren-5-yl acetate.

Step 3

A mixture of the product of Step 2 (4.3 g), 4'-(4-trans-pentylcyclohexyl)-N-(4-(4,4,5,5-tetramethyl-1,3,2-dioxaborolan-2-yl)phenyl)-[1,1'-biphenyl]-4-carboxamide (4.94 g), sodium carbonate (4 g), THF (200 mL), water (20 mL) and tetrakis(triphenylphosphine)palladium(0) (1 g) was placed in a reaction flask and degassed by bubbling nitrogen through the mixture for 10 minutes. The mixture was then heated to reflux for 17 hours. Then to the reaction mixture, potassium carbonate (5 g) and ethanol (50 ml) were added. After refluxing for another 8 hours, THF (200 mL) and sodium chloride saturated water (200 mL) were added. The resulting organic layer was collected, washed with 100 ml 1 N HCl three times, washed with 100 mL 1 N sodium sulfite water solution once, washed with sodium chloride saturated water once, dried over magnesium sulfate and concentrated. The obtained residue was dissolved in 10/1 toluene/THF (200 mL) and then passed through a silica gel plug column and eluted with 10/1 toluene/THF. The obtained clear solution was concentrated and stirred in methanol for half an hour. The resulting solid was collected and dried. Off-white solid (7.5 g) was obtained as the product. NMR indicated that the product had a structure consistent with N-(4-(2,4-dichloro-5-hydroxy-9-methoxy-7,7-dimethyl-7H-benzo[c]fluoren-10-yl)phenyl)-4'-(4-trans-pentylcyclohexyl)-[1,1'-biphenyl]-4-carboxamide.

Step 4

The product of Step 3 (3 g), 1-(4-butoxyphenyl)-1-(4-methoxyphenyl)prop-2-yn-1-ol (1.8 g), p-toluenesulfonic acid (73 mg) and dichloroethane (50 ml) were placed in a reaction flask. The mixture was stirred and refluxed for 4 hours. All solvent was removed. The product was purified by CombiFlash® Rf from Teledyne ISCO. A black solid (2 g) was obtained as the product. NMR indicated that the structure was consistent with 3-(4-butoxyphenyl)-3-(4-methoxyphenyl)-10-[4-(4-(4-(4-trans-pentylcyclohexyl)phenyl)benzamido)phenyl]-5,7-dichloro-11-methoxy-13,13-dimethyl-3H,13H-indeno[2',3':3,4]naphtho[1,2-b]pyran.

Example 6

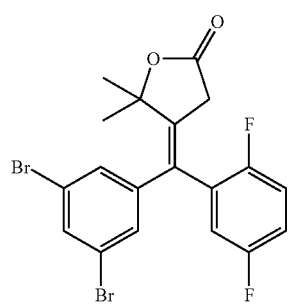 [SMILES: CC1(C)OC(=O)C/C1=C(/c1cc(Br)cc(Br)c1)c1cc(F)ccc1F]

Procedures from Step 1 to Step 3 of Example 1 were followed except that 2,5-difluorobenzoyl chloride was used in place of 4-trifluoromethylbenzoyl chloride in step 1. White solid was obtained as the product. NMR indicated that the product had a structure consistent with a mixture of E/Z isomer of beta-((3,5-dibromophenyl)(2,5-difluorophenyl)methylene)-gamma,gamma-dimethyl-gamma-butyrolactone.

Example 6A

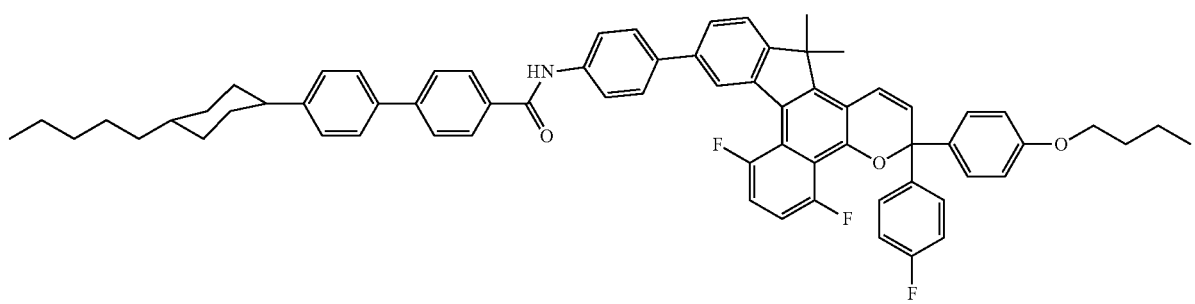 [SMILES: CCCCCC1CCC(c2ccc(-c3ccc(C(=O)Nc4ccc(-c5ccc6c(c5)-c5c(c7c(c8c(F)ccc(F)c58)OC(c5ccc(F)cc5)(c5ccc(OCCCC)cc5)C=C7)C6(C)C)cc4)cc3)cc2)CC1]

Step 1

Using the product from Example 6, the procedure from Step 1 of Example 1A was followed. White crystals were obtained as the product. NMR indicated that the product had a structure consistent with 8,10-dibromo-1,4-difluoro-7,7-dimethyl-7H-benzo[c]fluoren-5-yl acetate.

Step 2

To a degassed solution of toluene (40 mL) and ethanol (40 mL) was added triphenylphosphine (0.32 g) and palladium acetate (0.1 g). The product of Step 1 (2.00 g) and 4'-(4-trans-pentylcyclohexyl)-N-(4-(4,4,5,5-tetramethyl-1,3,2-dioxaborolan-2-yl)phenyl)-[1,1'-biphenyl]-4-carboxamide (2.22 g) were added and the solution was degassed for 10 min. Potassium carbonate (1.67 g) was added and the resulting mixture was heated to reflux for 6 h. The reaction mixture was cooled to room temperature and diluted with ethyl acetate (200 mL). The mixture was filtered through a bed of CELITE® filter aid and the filtrate was collected and concentrated to provide a residue. The residue was purified by silica gel column separation using 19/1 toluene/ethyl acetate as the eluent. To the resulting cream colored residue, toluene was added to precipitate the product. The resulting precipitate was collected by vacuum filtration and dried to provide a cream colored solid (0.6 g).

Step 3

The procedure from Step 3 of Example 1A was followed except that 1-(4-butoxyphenyl)-1-(4-fluorophenyl)prop-2-yn-1-ol and the product of Step 2 were used in place of 1-(4-methoxyphenyl)-1-phenylprop-2-yn-1-ol and the product of Step 2 of Example 1A. NMR analysis of the obtained solid indicated a structure that was consistent with 3-(4-butoxyphenyl)-3-(4-fluorophenyl)-10-[4-(4-(4-(4-trans-pentylcyclohexyl)phenyl)benzamido)phenyl]-5,8-difluoro-13,13-dimethyl-3H,13H-indeno[2',3':3,4]naphtho[1,2-b]pyran.

Example 7

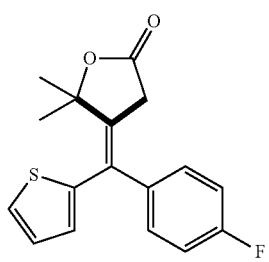

Procedures from Step 2 to Step 3 of Example 1 were followed except that (4-fluorophenyl)(thien-2-yl) ketone was used in place of 3,5-dibromo-4'-trifluoromethylbenzophenone in step 2. Oil was obtained as the product. NMR indicated that the product had a structure consistent with a mixture of E/Z isomer of beta-((4-fluorophenyl)(thiophen-2-yl)methylene)-gamma,gamma-dimethyl-gamma-butyrolactone.

Example 7B

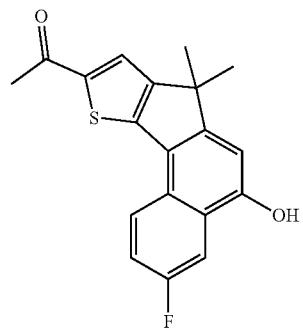 [SMILES: CC(=O)c1cc2c(s1)-c1c(cc(O)c3cc(F)ccc13)C2(C)C]

Using the product from Example 7, procedures from Steps 1 and 2 of Example 1A were followed. NMR indicated that the obtained black solid product had a structure consistent with 1-(3-fluoro-5-hydroxy-7,7-dimethyl-7H-benzo[6,7]indeno[1,2-b]thiophen-9-yl)ethanone.

Example 8

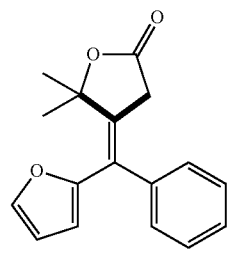

Procedures from Step 2 to Step 3 of Example 1 were followed except that furan-2-yl(phenyl)methanone, which was prepared following a literature procedure using a Friedel-Crafts reaction (Sarvari, M. H.; Sharghi, H. J. Org. Chem. 2004, 69, 6953-6956), was used in place of 3,5-dibromo-4'-trifluoromethylbenzophenone in Step 2. Oil was obtained as the product. NMR indicated that the product had a structure consistent with a mixture of E/Z isomer of beta-(phenyl(furan-2-yl)methylene)-gamma,gamma-dimethyl-gamma-butyrolactone.

Part 2: Photochromic Performance Testing and Results

The photochromic performance of the photochromic materials of Examples 1A-6A were tested as follows. A quantity of the photochromic material to be tested, calculated to yield a $1.5 \times 10^{-3}$ M solution, was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis (2-methyl propionitrile) (AIBN). The photochromic material was dissolved into the monomer blend by stirring and gentle heating if necessary. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for over a 2 hour interval. After the mold was opened, the polymer sheet was cut using a utility knife to score the surface and snap into 2 inch (5.1 cm) test squares.

The photochromic test squares prepared as described above were tested for photochromic response on an optical bench. Prior to testing on the optical bench, the photochromic test squares were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.).

The optical bench fitted with a Schott 3 mm KG-2 band-pass filter, neutral density filter(s) and a Newport Model#67005 300-watt Xenon arc lamp with Model#69911 power supply in association with a Newport Model 689456 Digital Exposure/Timer was used to control the intensity of the irradiance beam utilized for activation of the sample. A Uniblitz model# CS25S3ZM0 with model# VMM-D3 controller) high-speed computer controlled shutter, a fused silica condensing lens for beam collimation of this activation lamp beam though a quartz glass water bath sample chamber.

A custom made broadband light source for monitoring response measurements was directed through the sample such that the angle between the activation source and the monitoring beam is 30 degrees with the sample positioned perpendicular to this monitoring beam. This broad beam light source is obtained by collecting and combining separately filtered light from a 100-Watt tungsten halogen lamp (controlled by a Lambda UP60-14 constant voltage powder supply) with a split-end, bifurcated fiber optical cable to enhance the short wavelength light intensity. After passing through the sample, this monitoring light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

The $\lambda_{max\text{-}vis}$ is the wavelength in the visible spectrum at which the maximum absorption of the activated-state form of the photochromic compound in a test square occurs. The $\lambda_{max\text{-}vis}$ wavelength was determined by testing the photochromic test squares in a Varian Cary 4000 UV-Visible spectrophotometer.

The change in Optical density at saturation for each test sample was determined by opening the shutter from the xenon lamp and measuring the transmittance after exposing the test chip to 3W/m2 UVA radiation for 30 minutes. The change in Optical density at saturation was calculated using the formula: $\Delta OD=\log(\% Tb/\% Ta)$, where % Tb is the percent transmittance in the bleached state, % Ta is the percent transmittance in the activated state both at the $\lambda_{max\text{-}vis}$ and the logarithm is to the base 10. The first fade half life ("$T_{1/2}$") or bleach rate is the time interval in seconds for the absorbance of the activated-state form of the photochromic material in the test squares to reach one half the $\Delta OD$ at saturation value at room temperature (23° C.), after removal of the source of activating light. The Sensitivity ($\Delta OD$/Min) is a measure of how quickly the sample darkens and is calculated from the equation $\Delta OD_{sen}=\Delta OD_{5min}\times 12$.

TABLE 1

Photochromic Performance Test Results

| Example # | $\lambda_{max\text{-}vis}$ (nm) | Sensitivity ($\Delta OD$/Min) | $\Delta OD$ at saturation | T ½ (sec) |
|---|---|---|---|---|
| 1A | 554 | 0.39 | 0.22 | 28 |
| 2A | 579 | 0.38 | 0.22 | 30 |
| 3A | 562 | 0.28 | 0.10 | 14 |
| 4A | 551 | 0.65 | 0.76 | 79 |
| 5A | 580 | 0.77 | 0.7 | 82 |
| 6A | 547 | 0.75 | 0.85 | 96 |

The present invention has been described with reference to specific details of particular embodiments thereof. It is not intended that such details be regarded as limitations upon the scope of the invention except insofar as and to the extent that they are included in the accompanying claims.

We claim:

1. A lactone compound selected from lactone compounds represented by at least one of the following Formula I and Formula II,

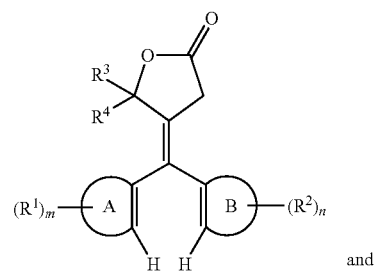

and

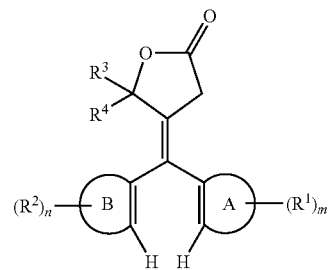

wherein Ring-A and Ring-B are each independently unsubstituted aryl, substituted aryl, unsubstituted fused ring aryl, substituted fused ring unsubstituted heteroaryl, or substituted heteroaryl, m and n are each independently selected from 0 to 4, $R^1$ for each m, and $R^2$ for each n, are in each case independently hydrocarbyl optionally interrupted with at least one of —O—, —S—, —N($R_{11}'$)— where $R_{11}'$ is, hydrocarbyl or substituted hydrocarbyl, or combinations of two or more thereof; substituted hydrocarbyl optionally interrupted with at least one of —O—, —S—, —N($R_{11}'$)— where $R_{11}'$ is, hydrocarbyl or substituted hydrocarbyl, or combinations of two or more thereof; halogen; or —N($R_{11}'$)$R_{12}'$, wherein $R_{11}'$ and $R_{12}'$ are each independently, hydrocarbyl or substituted hydrocarbyl, or $R_{11}'$ and $R_{12}'$ together form a ring structure optionally including at least one heteroatom, and $R^3$ and $R^4$ each independently represents hydrocarbyl optionally interrupted with at least one of —O—, —S—, and —N($R_{11}'$)— where $R_{11}'$ is hydrocarbyl or substituted hydrocarbyl; or substituted hydrocarbyl optionally interrupted with at least one of —O—, —S—, and —N($R_{11}'$)— where $R_{11}'$ is hydrocarbyl or substituted hydrocarbyl; or $R^3$ and $R^4$ together form a ring structure optionally including at least one heteroatom.

2. The lactone compound of claim 1 wherein,

Ring-A and Ring-B are each independently selected from unsubstituted aryl and substituted aryl;

$R^1$ for each m, and $R^2$ for each n, are in each case independently, halogen selected from fluoro, iodo, bromo and chloro;

$C_1$-$C_{20}$ alkyl;

$C_3$-$C_{10}$ cycloalkyl;

substituted or unsubstituted phenyl, the phenyl substituents being selected from halogen, halo($C_1$-$C_{20}$)alkyl, $C_1$-$C_{20}$ alkyl or $C_1$-$C_{20}$ alkoxy;

—O—$R_{10}'$ wherein $R_{10}'$ is $C_1$-$C_{20}$ alkyl, phenyl($C_1$-$C_{20}$) alkyl, mono($C_1$-$C_{20}$)alkyl substituted phenyl($C_1$-$C_{20}$) alkyl, mono($C_1$-$C_{20}$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl;

—N($R_{11}'$)$R_{12}'$, wherein $R_{11}'$ and $R_{12}'$ are each independently $C_1$-$C_{20}$ alkyl, phenyl, naphthyl, furanyl, benzofuran-2-yl benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}'$ and $R_{12}'$ come together with the nitrogen atom to form a $C_3$-$C_{20}$ hetero-bicycloalkyl ring or a $C_4$-$C_{20}$ hetero-tricycloalkyl ring;

a nitrogen containing ring represented by the following graphic formula XIIA,

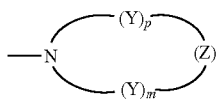

XIIA wherein each —Y— is independently chosen for each occurrence from —$CH_2$—, —CH($R_{13}'$)—, —C($R_{13}'$)$_2$—, —CH(aryl)-, —C(aryl)$_2$—, and —C($R_{13}'$)(aryl)-, and Z is —Y—, —O—, —S—, —N($R_{13}'$)—, or —N(aryl)—, wherein each $R_{13}'$ is independently $C_1$-$C_{20}$ alkyl, each aryl is independently phenyl or naphthyl, m is an integer 1, 2 or 3, and p is an integer 0, 1, 2, or 3 and provided that when p is 0, Z is —Y—; a group represented by one of the following graphic formulas XIIB or XIIC,

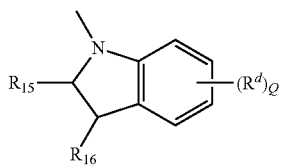

XIIB

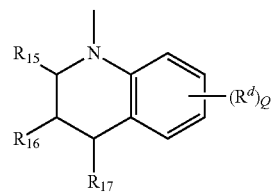

XIIC wherein $R_{15}$, $R_{16}$, and $R_{17}$ are each independently hydrogen, $C_1$-$C_{20}$ alkyl, phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl, $C_1$-$C_{20}$ alkoxy, fluoro or chloro, and Q is an integer 0, 1, 2, or 3; and unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_{20}$ alkyl, $C_1$-$C_{20}$ alkoxy, or phenyl($C_1$-$C_{20}$)alkyl; or two adjacent $R^1$ groups, or two adjacent $R^2$ groups, independently together form a group represented by one of XIID and XIIE:

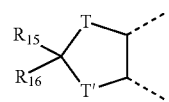

XIID

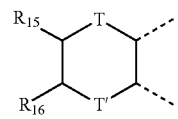

XIIE wherein T and T' are each independently oxygen or the group —$NR_{11}'$—, where $R_{11}'$, $R_{15}$, and $R_{16}$ are as set forth above; and $R^3$ and $R^4$ are as set forth above.

3. The lactone compound of claim 1, wherein $R^1$ for each m, and $R^2$ for each n, are in each case independently $C_1$-$C_6$ alkyl, $C_3$-$C_7$ cycloalkyl, $C_1$-$C_8$ haloalkyl, fluoro, iodo, Promo, chloro, or —O—$R_{10}'$.

4. The lactone compound of claim 3, wherein $R^3$ and $R^4$ each independently represents $C_1$-$C_8$ alkyl, $C_1$-$C_8$ haloalkyl, and $C_3$-$C_7$ cycloalkyl, or $R^3$ and $R^4$ together form a spiro substituent selected from a substituted or unsubstituted spirocarbocyclic ring containing 3 to 6 carbon atoms.

5. The lactone compound of claim 1, wherein said lactone compound is selected from lactone compounds represented by at least one of the following Formula Ia and Formula IIa,

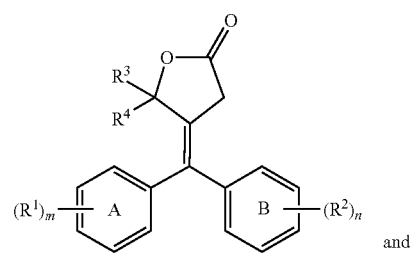

Ia and

IIa
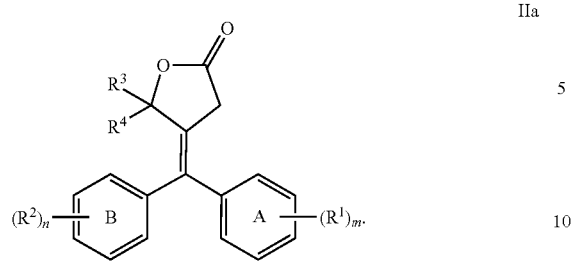
* * * * *